United States Patent
Uchiyama

(10) Patent No.: US 9,551,794 B2
(45) Date of Patent: Jan. 24, 2017

(54) RADIATION IMAGING SYSTEM, RADIATION IMAGING APPARATUS, AND METHOD OF CONTROLLING THE SAME

(71) Applicant: CANON KABUSHIKI KAISHA, Tokyo (JP)

(72) Inventor: Akehiko Uchiyama, Kawasaki (JP)

(73) Assignee: CANON KABUSHIKI KAISHA, Tokyo (JP)

(*) Notice: Subject to any disclaimer, the term of this patent is extended or adjusted under 35 U.S.C. 154(b) by 703 days.

(21) Appl. No.: 13/901,634

(22) Filed: May 24, 2013

(65) Prior Publication Data

US 2013/0322597 A1    Dec. 5, 2013

(30) Foreign Application Priority Data

Jun. 5, 2012  (JP) ................................. 2012-128403
Mar. 14, 2013  (JP) ................................. 2013-052433

(51) Int. Cl.
| | | |
|---|---|---|
| *G01T 1/17* | (2006.01) | |
| *H04N 5/32* | (2006.01) | |
| *G01N 23/04* | (2006.01) | |

(52) U.S. Cl.
CPC .......... *G01T 1/17* (2013.01); *H04N 5/32* (2013.01); *G01N 23/04* (2013.01)

(58) Field of Classification Search
CPC ........... A61B 6/4233; G01T 1/17; H04N 5/32; H04N 5/361; H04N 5/378; H04N 5/335; G01N 23/04

See application file for complete search history.

(56) References Cited

U.S. PATENT DOCUMENTS

2010/0195796 A1* 8/2010 Takahashi ............... H01J 35/06
                                                        378/92
2010/0295976 A1* 11/2010 Kyushima .............. H04N 5/335
                                                        348/246

(Continued)

FOREIGN PATENT DOCUMENTS

| JP | A 2003-033340 | 2/2003 |
|---|---|---|
| JP | A 2011-174908 | 9/2011 |

(Continued)

OTHER PUBLICATIONS

Machine Translation of WO2011/135917.*
Office Action issued Mar. 31, 2014 in counterpart Japanese patent application 2013-052433, with translation.

*Primary Examiner* — Glen Kao
(74) *Attorney, Agent, or Firm* — Fitzpatrick, Cella, Harper & Scinto

(57) ABSTRACT

User-friendliness of a radiation imaging apparatus configured to reset a sensor array is improved. This invention is a radiation imaging apparatus including a two-dimensional sensor array. This apparatus includes a scan control signal generation circuit which controls the reset operation of the two-dimensional sensor array, a row number register which stores the row number of a line currently subjected to the reset operation at the time of detection of radiation irradiation, a scan control signal generation circuit which controls read operation after the completion of the radiation irradiation, and an image processing circuit which interpolates an image, of the image generated based on the signals read by the read operation, which corresponds to a line corresponding to the row number stored in the row number register, by using images of adjacent lines.

31 Claims, 23 Drawing Sheets

(56) References Cited

U.S. PATENT DOCUMENTS

| | | | |
|---|---|---|---|
| 2011/0180717 A1 | 7/2011 | Okada | 250/370.08 |
| 2012/0074332 A1* | 3/2012 | Watanabe | G01T 1/243 |
| | | | 250/394 |
| 2012/0132810 A1 | 5/2012 | Uchiyama | 250/358.1 |
| 2013/0032696 A1 | 2/2013 | Tajima | 250/208.1 |

FOREIGN PATENT DOCUMENTS

| | | | |
|---|---|---|---|
| JP | WO 2011135917 A1 * | 11/2011 | A61B 6/42 |
| JP | A 2011-249891 | 12/2011 | |
| JP | A 2012-070201 | 4/2012 | |
| WO | WO 2011/135917 A | 11/2011 | |

* cited by examiner

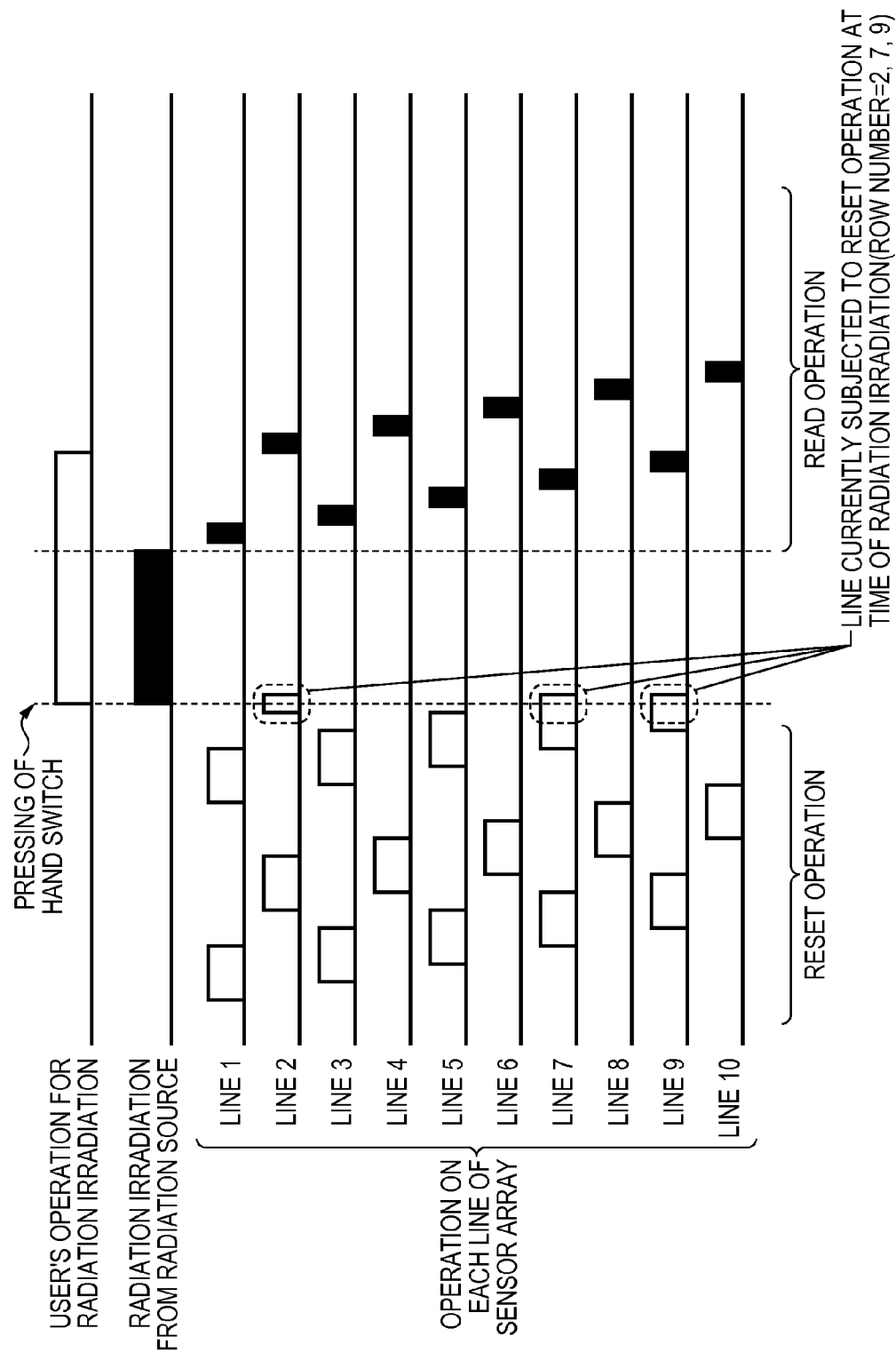

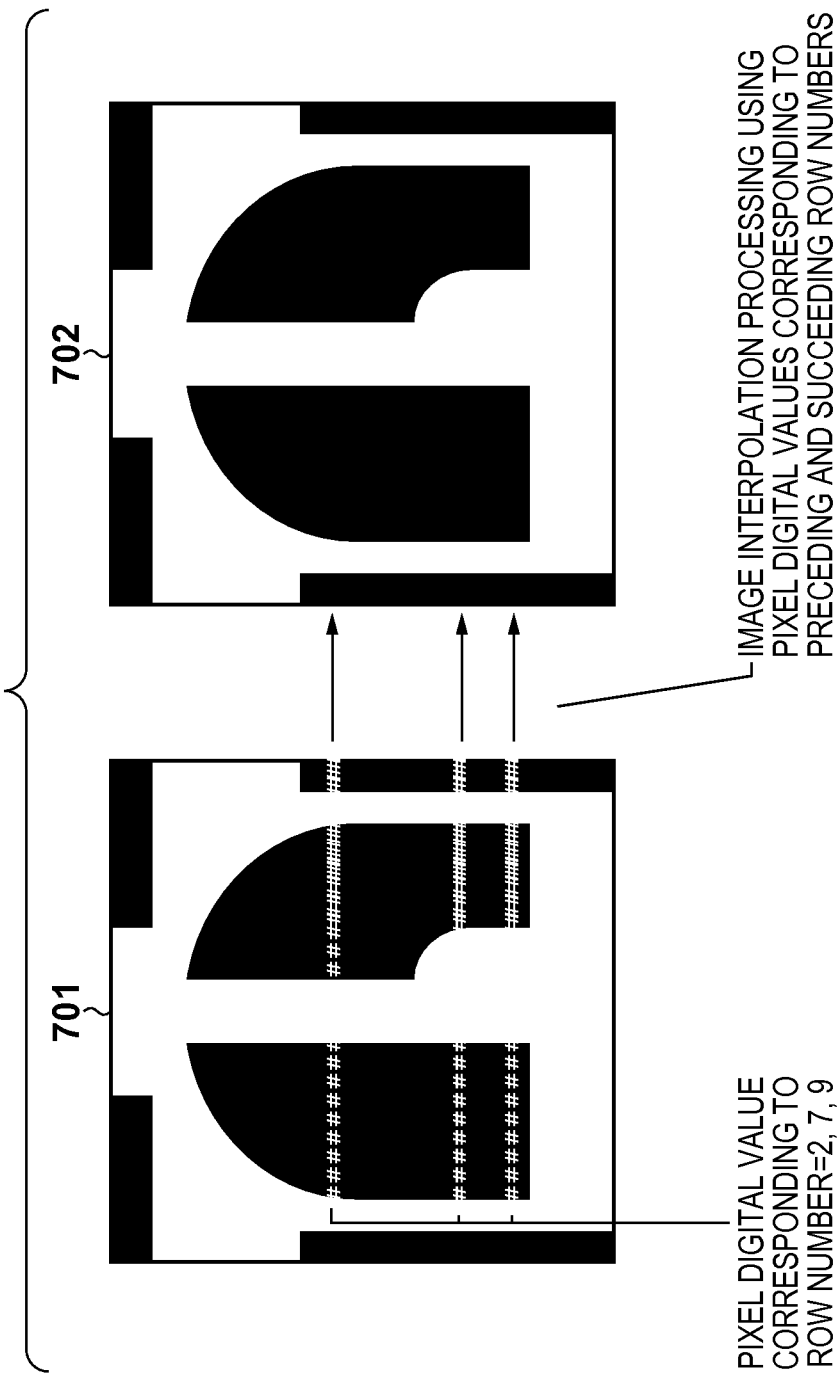

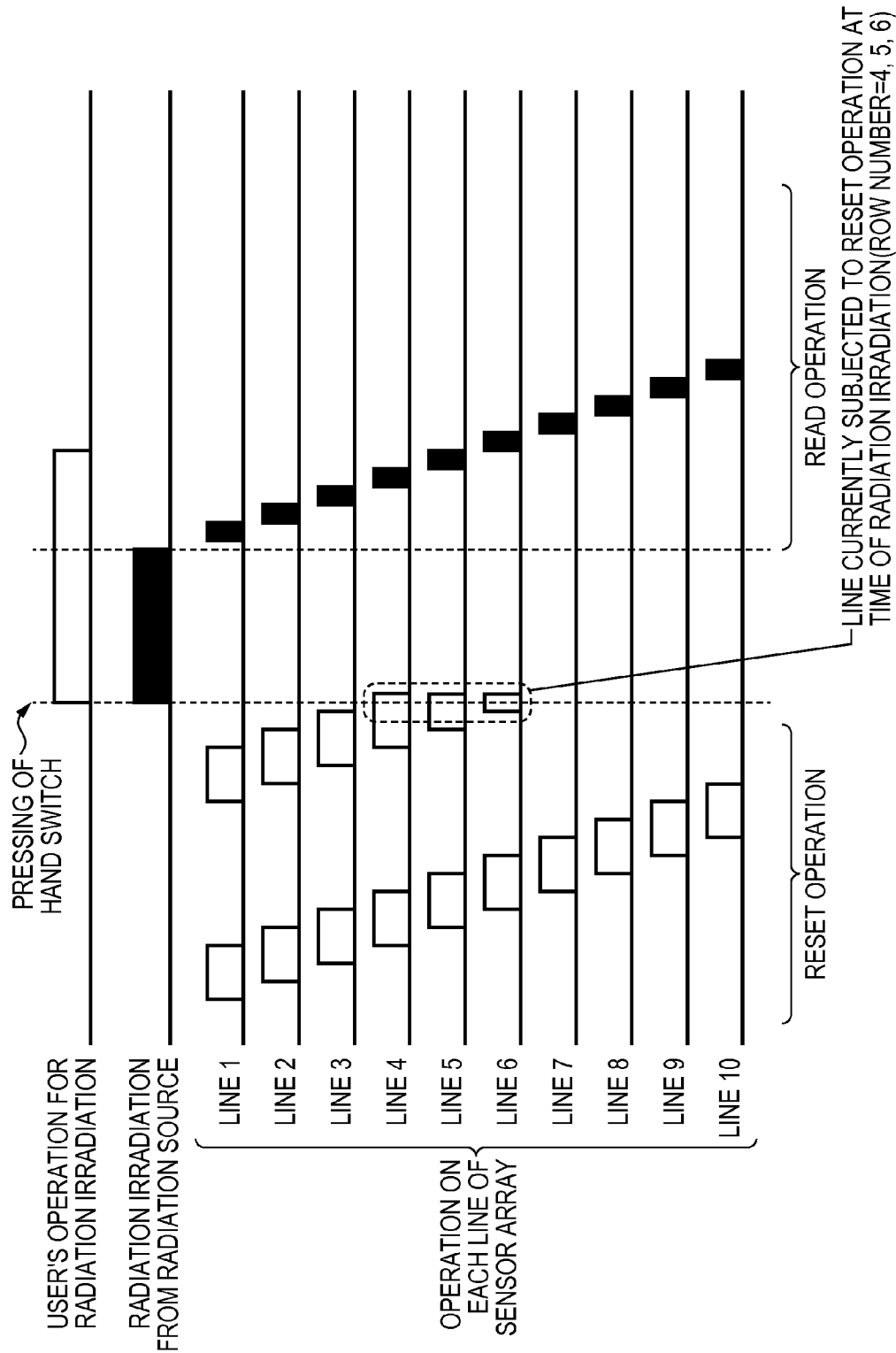

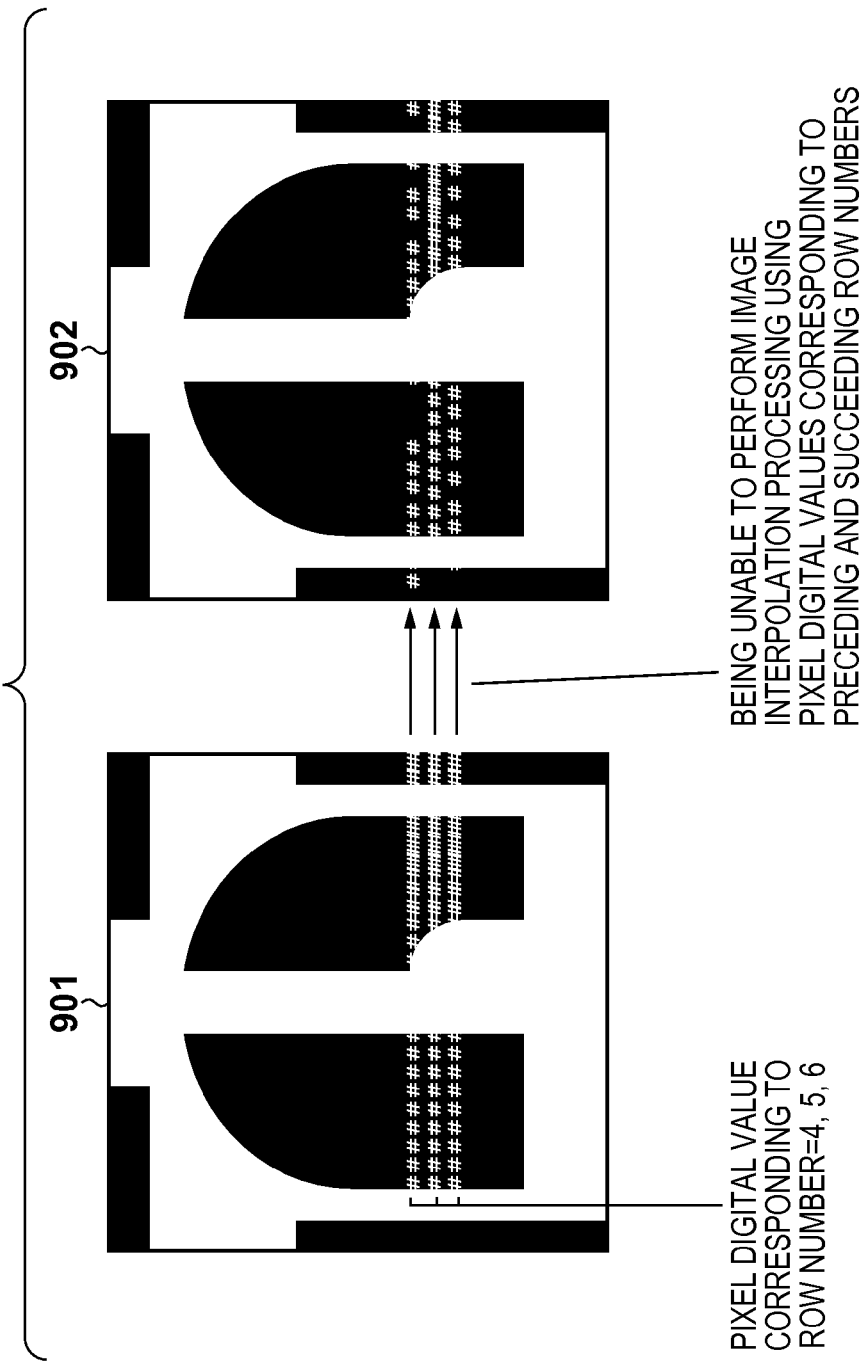

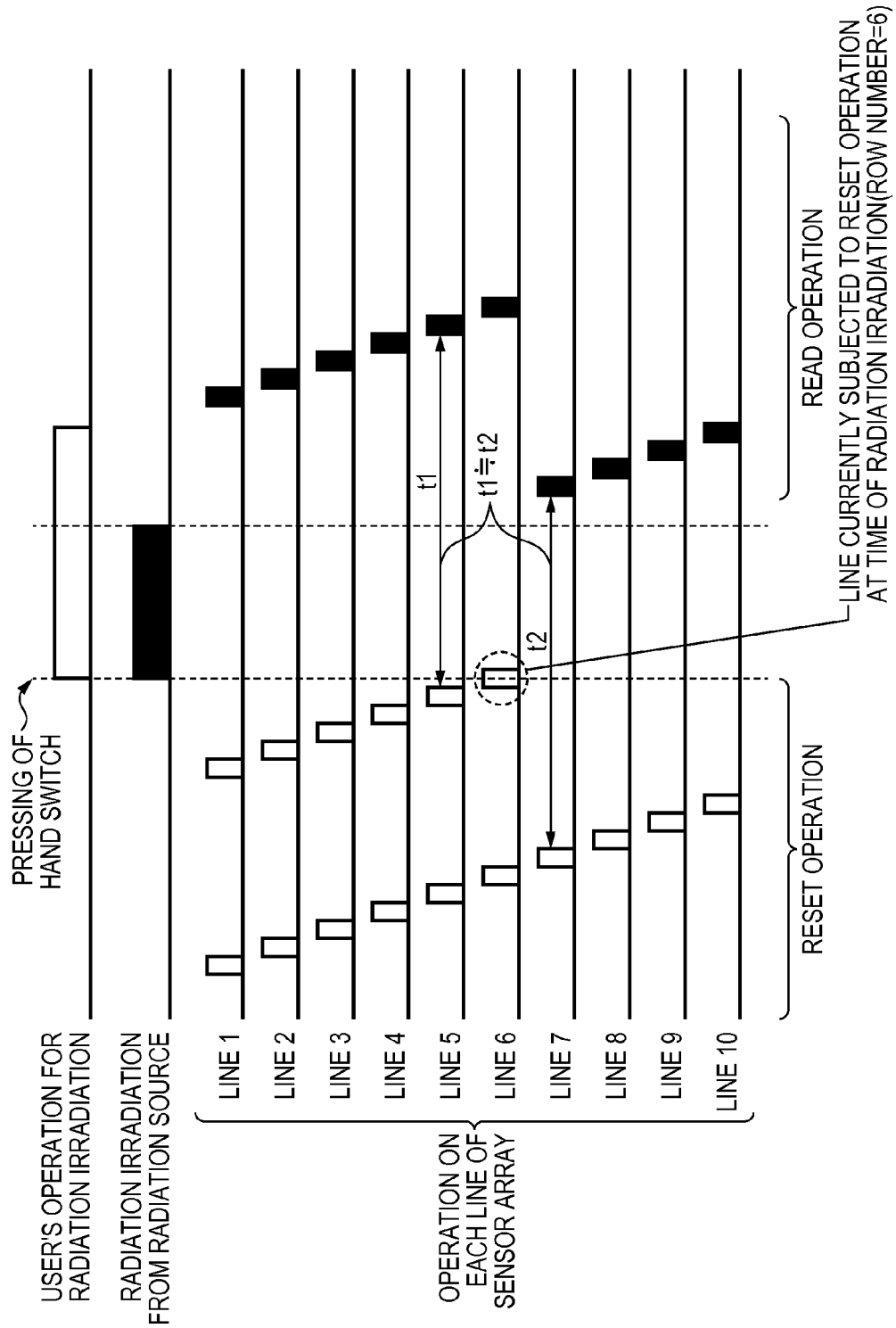

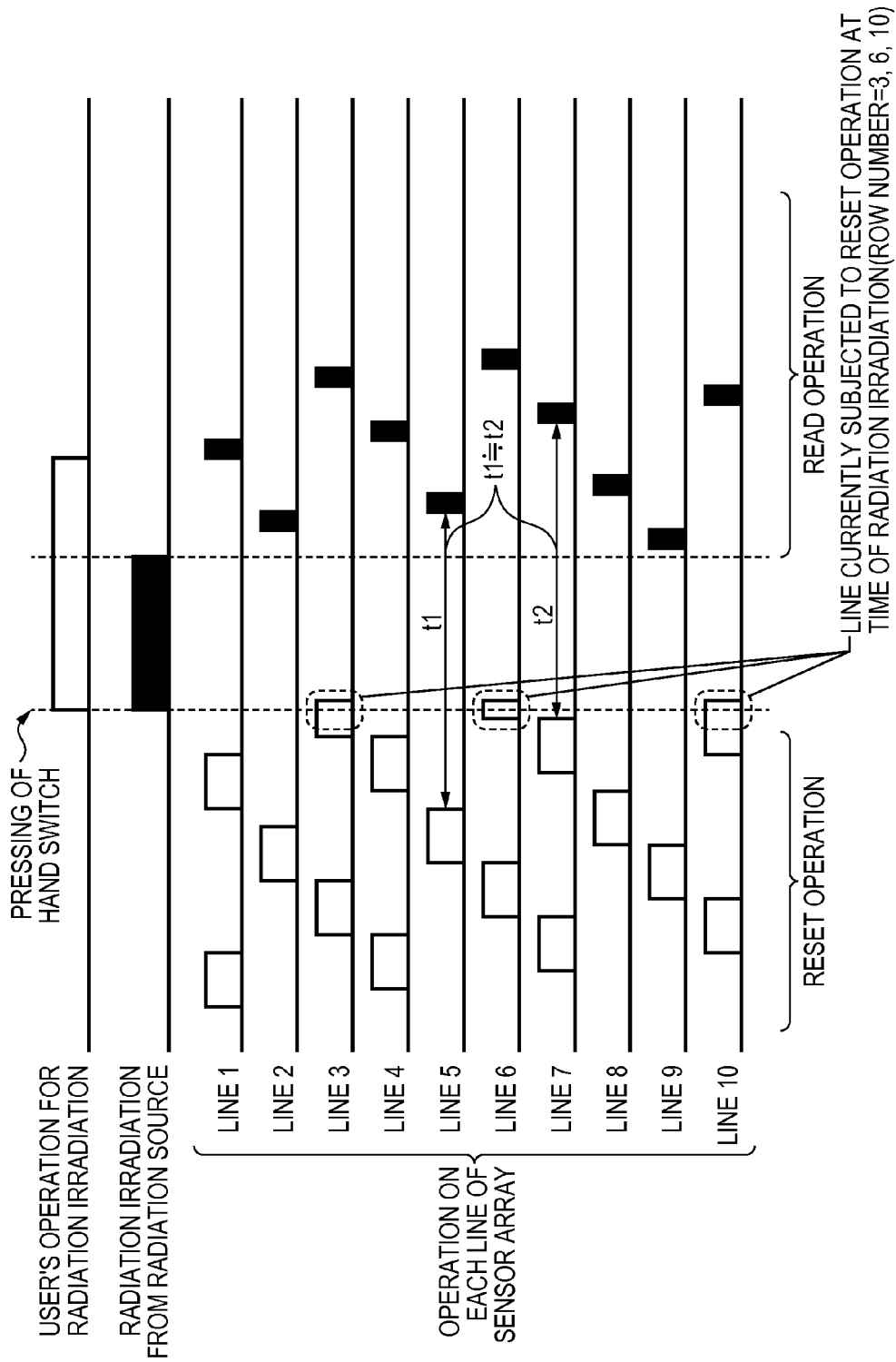

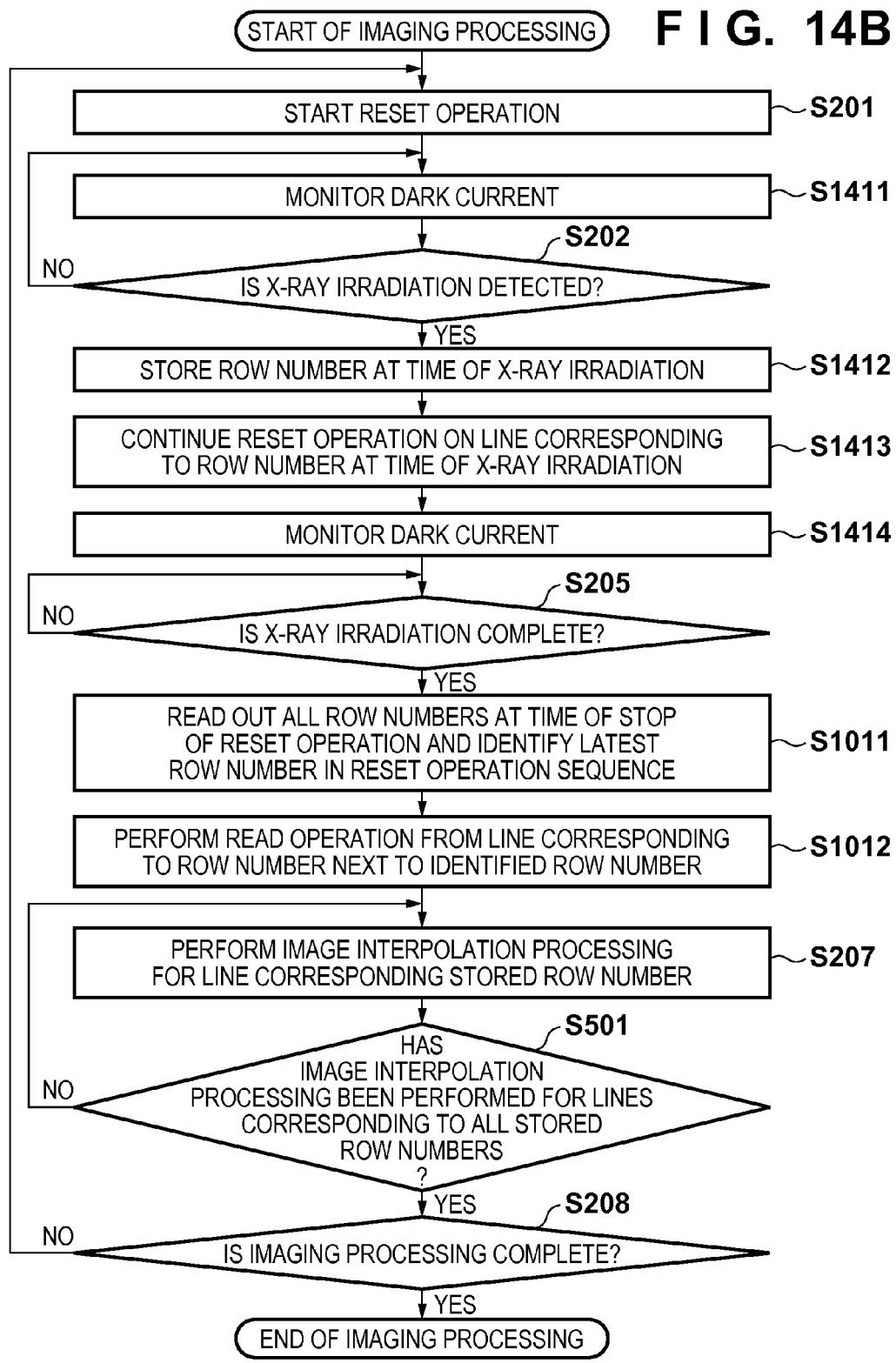

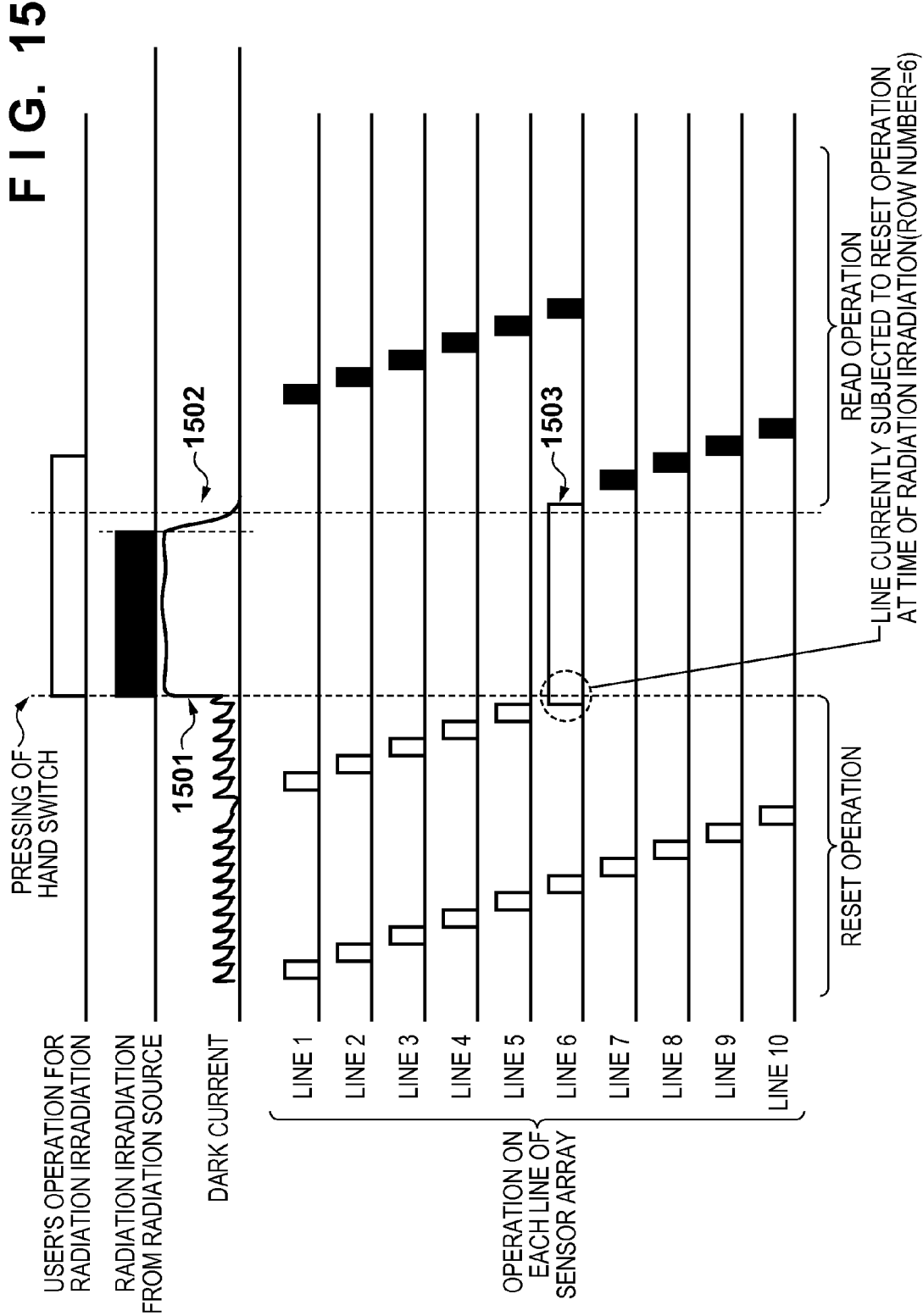

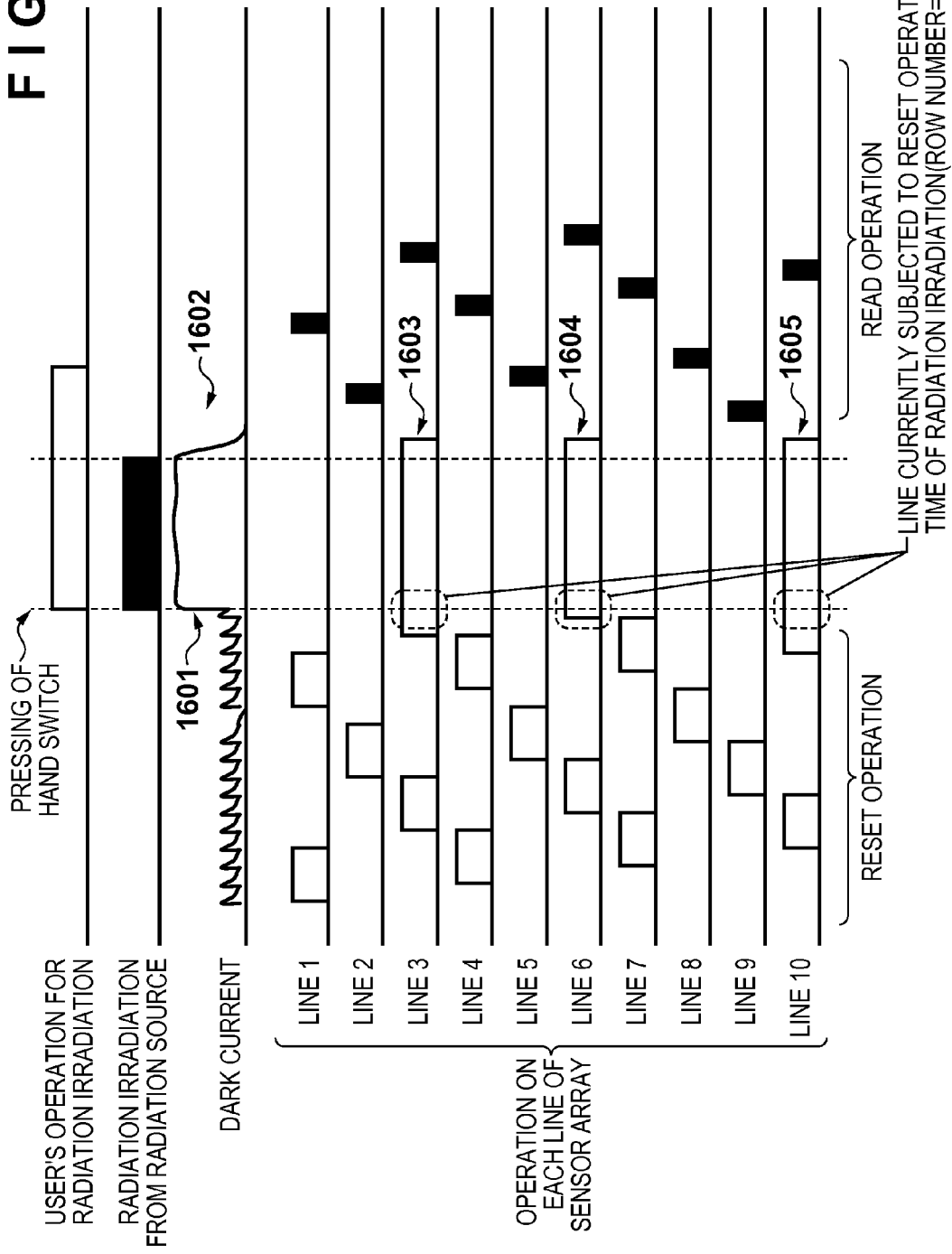

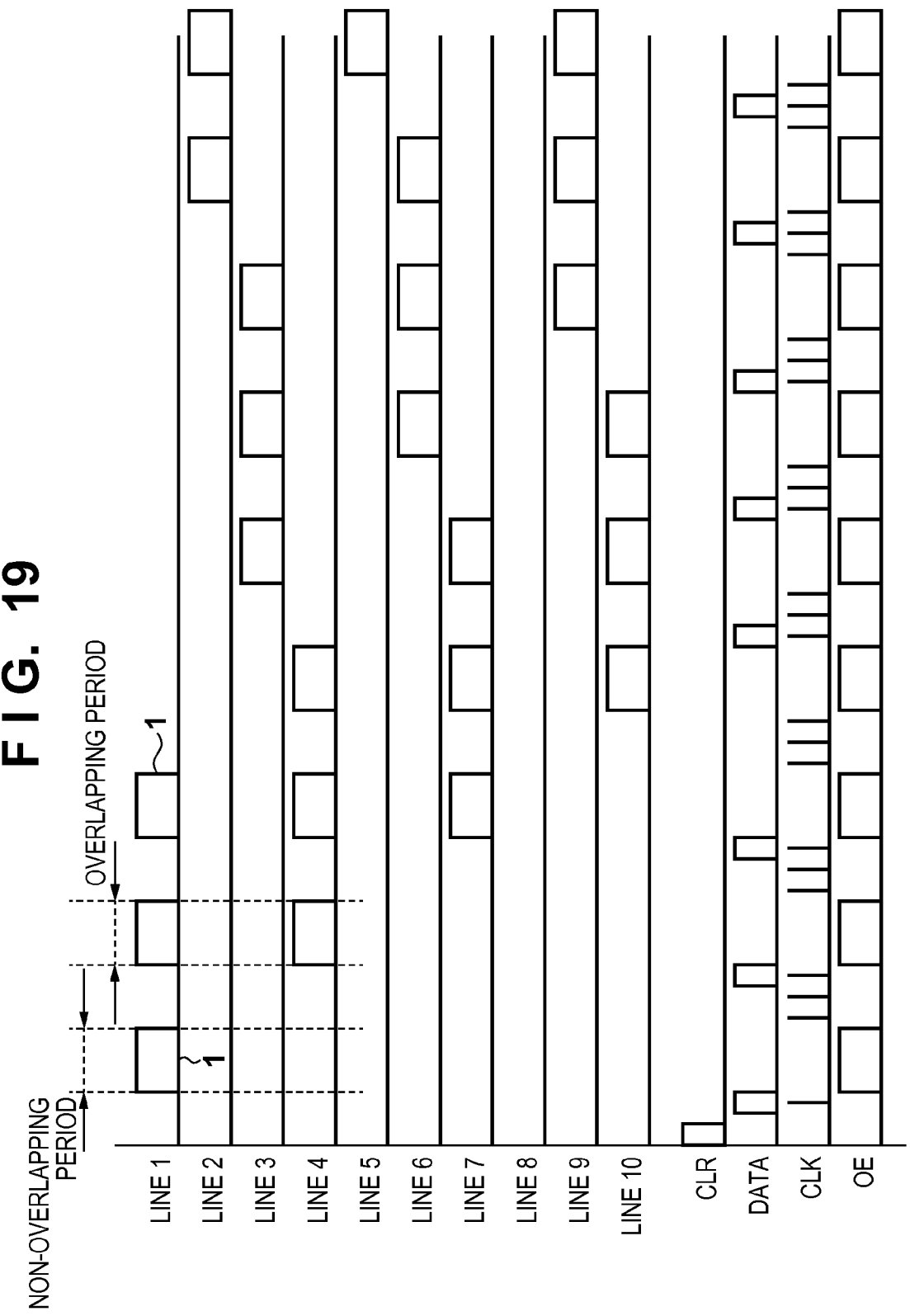

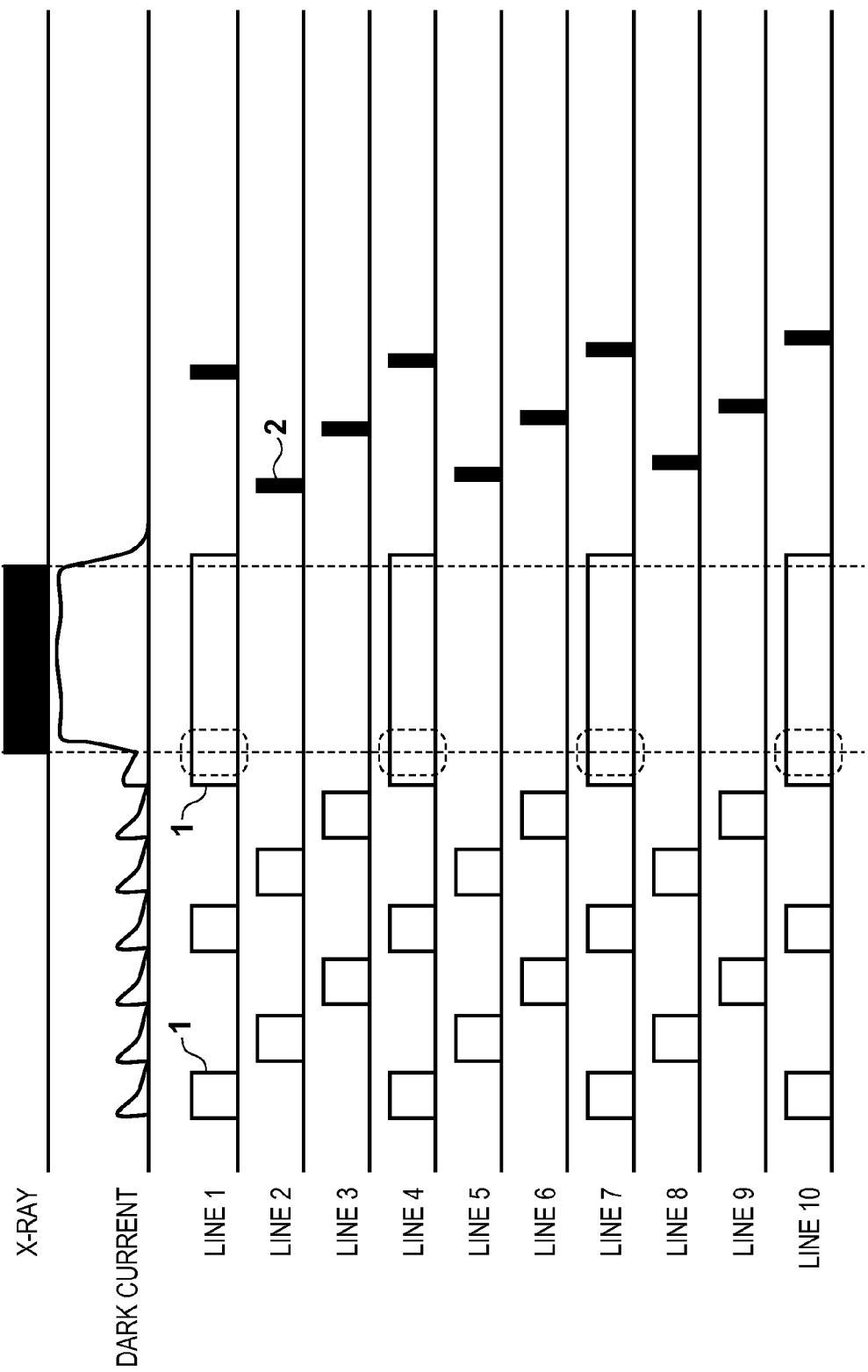

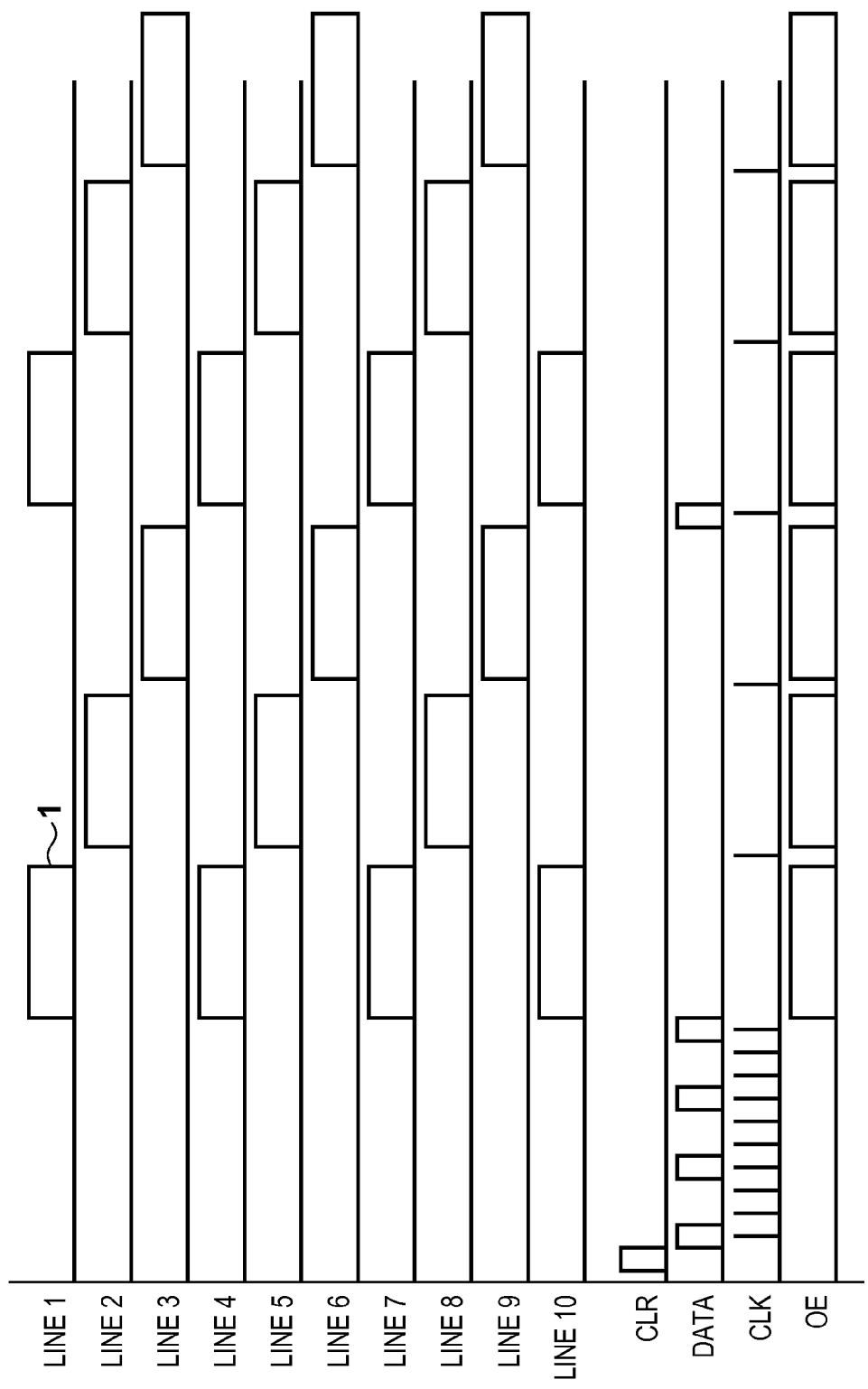

RADIATION IMAGING SYSTEM, RADIATION IMAGING APPARATUS, AND METHOD OF CONTROLLING THE SAME

BACKGROUND OF THE INVENTION

Field of the Invention

The present disclosure relates to a radiation imaging system, a radiation imaging apparatus, and a method of controlling the same.

Description of the Related Art

There has been a flat panel type radiation imaging apparatus provided with a sensor array formed by two-dimensionally arraying a plurality of pixels. Each pixel used for such a radiation imaging apparatus generally includes a conversion element which is obtained by forming a film on a glass substrate by using amorphous silicon or polysilicon as a material and converts radiation into an electrical signal and a switch element such as a TFT for transferring the electrical signal to the outside. In general, such a radiation imaging apparatus performs read operation by transferring, to a reading apparatus, the signals converted by conversion elements upon performing matrix driving using switch elements such as TFTs.

Each conversion element on the sensor array directly or indirectly generates a signal upon being irradiated with radiation. In a sensor array configured to indirectly generate signals, the conversion element of each pixel detects visible light converted from radiation by a phosphor instead of directly detecting radiation. In a sensor array based on either the direct detection scheme or the indirect detection scheme, each pixel generates a signal with a certain level even in the total absence of radiation. In this case, this signal will be referred to as a "dark current".

Dark currents have different characteristics in the respective pixels on the sensor array. If dark currents are superimposed on the image signals obtained by radiation irradiation, uneven offsets are added to an image, resulting in a deterioration in image quality. In order to prevent this, the radiation imaging apparatus is configured to extract dark current charges from the sensor array periodically and/or intensively immediately before radiation irradiation by using a period during which no radiation is irradiated.

In this case, when extracting a dark current, if an image signal is superimposed on the dark current, it is not possible to separate them and extract only the dark current. That is, executing dark current extraction during radiation irradiation or in the interval after radiation irradiation and before reading of an image signal will lose the image signal. Therefore, in the radiation imaging apparatus, it is necessary to perform control so as to exclusively execute dark current extraction and radiation irradiation. For this reason, a synchronization mechanism for establishing synchronization is provided between the apparatus and a radiation source.

Depending on the scheme, some conversion element needs to periodically perform reset operation as well as dark current extraction. In this case as well, reset operation leads to the loss of an image signal, and requires exclusive control with respect to radiation irradiation.

SUMMARY OF THE INVENTION

The radiation imaging apparatus according to the embodiment of the present invention has the following arrangement. That is, a radiation imaging apparatus including a sensor array, comprising: first control unit configured to control reset operation of sequentially removing signals respectively output from a plurality of lines constituting the sensor array; identifying unit configured to identify a line currently subjected to the reset operation when a start of radiation irradiation is detected; second control unit configured to control read operation of reading a signal output from each of the plurality of lines at a timing set in advance for each line upon completion of the radiation irradiation; and interpolation unit configured to interpolate an image, which is part of an image generated based on signals read by the read operation, and which corresponds to a line identified by the identifying unit, by using images of adjacent lines.

In addition, another radiation imaging apparatus according to the embodiment of the present invention has, for example, the following arrangement. That is, a radiation imaging apparatus including a sensor array, comprising: control unit configured to sequentially read signals respectively output from a plurality of lines constituting the sensor array; identifying unit configured to identify a line currently subjected to the read operation when a start of radiation irradiation is detected; and interpolation unit configured to interpolate an image, which is part of an image generated based on signals read by the control unit after completion of the radiation irradiation, and which corresponds to a line identified by the identifying unit, by using images of adjacent lines.

A method of controlling a radiation imaging apparatus according to the embodiment of the present invention has, for example, the following arrangement. That is, a method of controlling a radiation imaging apparatus including a sensor array, comprising: a first control step of controlling reset operation of sequentially removing signals respectively output from a plurality of lines constituting the sensor array; an identifying step of identifying a line currently subjected to the reset operation when a start of radiation irradiation is detected; a second control step of controlling read operation of reading a signal output from each of the plurality of lines at a timing set in advance for each line upon completion of the radiation irradiation; and an interpolation step of interpolating an image, which is part of an image generated based on signals read by the read operation, and which corresponds to a line identified in identifying step, by using images of adjacent lines.

Further features of the embodiment of the present invention will become apparent from the following description of exemplary embodiments (with reference to the attached drawings).

BRIEF DESCRIPTION OF THE DRAWINGS

The accompanying drawings, which are incorporated in and constitute a part of the specification, illustrate embodiments of the invention and, together with the description, serve to explain the principles of the embodiments of the invention.

FIG. 6 is a timing chart showing a procedure for imaging processing by the radiation imaging apparatus 100;

FIG. 7 is a view for explaining image interpolation processing by the image processing circuit 133;

FIG. 8 is a timing chart for explanation in contrast with FIG. 6;

FIG. 9 is a view for explanation in contrast with FIG. 7;

FIG. 11 is a timing chart showing a procedure for imaging processing by the radiation imaging apparatus 100;

FIG. 12 is a timing chart showing a procedure for imaging processing by the radiation imaging apparatus 100;

FIG. 14B is a flowchart showing a procedure for imaging processing by the radiation imaging apparatus 1300;

FIG. 15 is a timing chart showing a procedure for imaging processing by the radiation imaging apparatus 1300;

FIG. 16 is a timing chart showing a procedure for imaging processing by the radiation imaging apparatus 1300;

FIG. 19 is a timing chart for explaining a control method for the shift register 122;

FIG. 20 is a timing chart for explaining the operation of the shift register 122; and FIG. 21 is a timing chart for explaining a control method for the shift register 122.

DESCRIPTION OF THE EMBODIMENTS

Embodiments of the present invention will now be described in detail in accordance with the accompanying drawings.

First Embodiment

1. Arrangement of Radiation Imaging Apparatus

Figure 1:
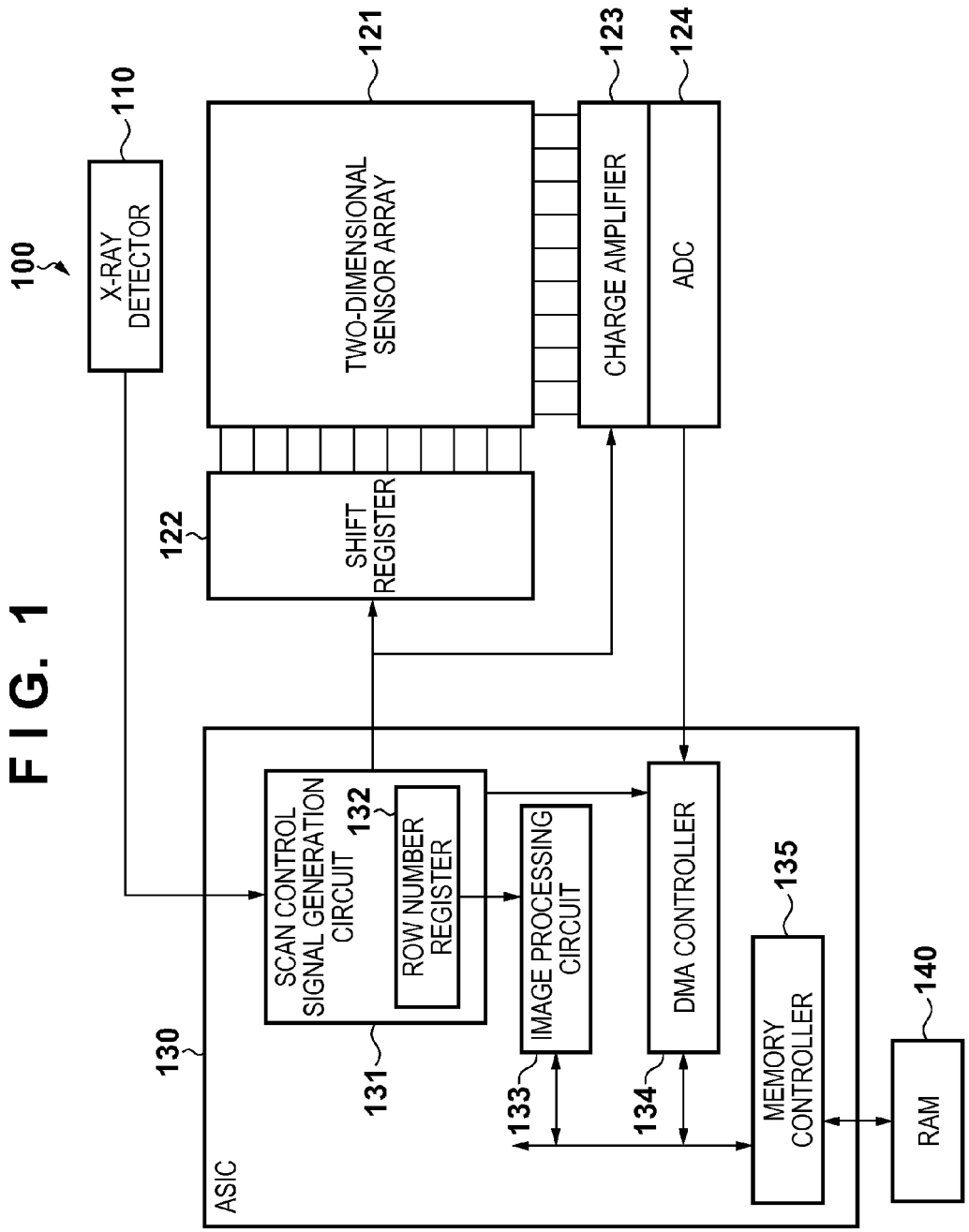
FIG. 1 is a block diagram showing the arrangement of a radiation imaging apparatus 100.

The arrangement of a radiation imaging apparatus according to the first embodiment of the present invention will be described first. FIG. 1 is a block diagram showing the arrangement of a radiation imaging apparatus 100 according to this embodiment. As shown in FIG. 1, the radiation imaging apparatus 100 includes a two-dimensional sensor array 121 as a receiver. A shift register 122 as a row selection means is connected to the two-dimensional sensor array 121. The shift register 122 sequentially selects the TFT switches on the two-dimensional sensor array 121 to scan the two-dimensional sensor array 121. Column signal lines connecting the respective column pixels are wired on the two-dimensional sensor array and are connected to a charge amplifier 123. It is possible to generate an image by measuring signals (charge amounts) flowing in the respective column signal lines using the charge amplifier while scanning the two-dimensional sensor array 121. Performing scanning while fixing the voltage of each column signal line to a specific value can perform the reset operation of removing dark currents.

The radiation imaging apparatus 100 is further equipped with an ASIC 130. A scan control signal generation circuit 131 in the ASIC 130 controls a sensor unit including the shift register 122 and the charge amplifier 123. The scan control signal generation circuit 131 includes a row number register 132 which stores row numbers. When reset operation is interrupted at an arbitrary timing, the row number register 132 can store the corresponding row number. When performing read operation, the apparatus starts the read operation from the line corresponding to a row number next to the row number stored in the row number register 132. After the read operation, the stored row number is transferred to an image processing circuit 133. In this manner, the scan control signal generation circuit 131 functions as the first control means for controlling reset operation and the second control means for controlling read operation.

An ADC (A/D Converter) 124 is connected to the charge amplifier 123. When performing read operation, the apparatus converts a signal (charge amount) on each column signal line measured by the charge amplifier 123 into a pixel digital value. The pixel digital value is transferred to a RAM 140 via a DMA controller 134 in the ASIC. Assume that when the DMA controller 134 transfers the pixel digital value onto the RAM 140, the apparatus has already adjusted the corresponding address upon reception of a command from the scan control signal generation circuit 131. Pixel digital values are arranged in the RAM 140 so as to reproduce the pixel arrangement on the two-dimensional sensor array.

The image processing circuit 133 in the ASIC 130 reads and computes the pixel digital values in the RAM 140. At this time, the image processing circuit 133 refers to the row number stored in the row number register 132 in the scan control signal generation circuit 131 described above and performs image interpolation processing concerning the line corresponding to the row number.

The radiation imaging apparatus 100 is further equipped with an X-ray detector 110 separately from the above sensor unit. This allows detection of the start and stop of X-ray irradiation. An output from the X-ray detector 110 is input to the ASIC 130. The scan control signal generation circuit 131 can identify an X-ray irradiation state.

2. Operation of Radiation Imaging Apparatus

Figure 2:
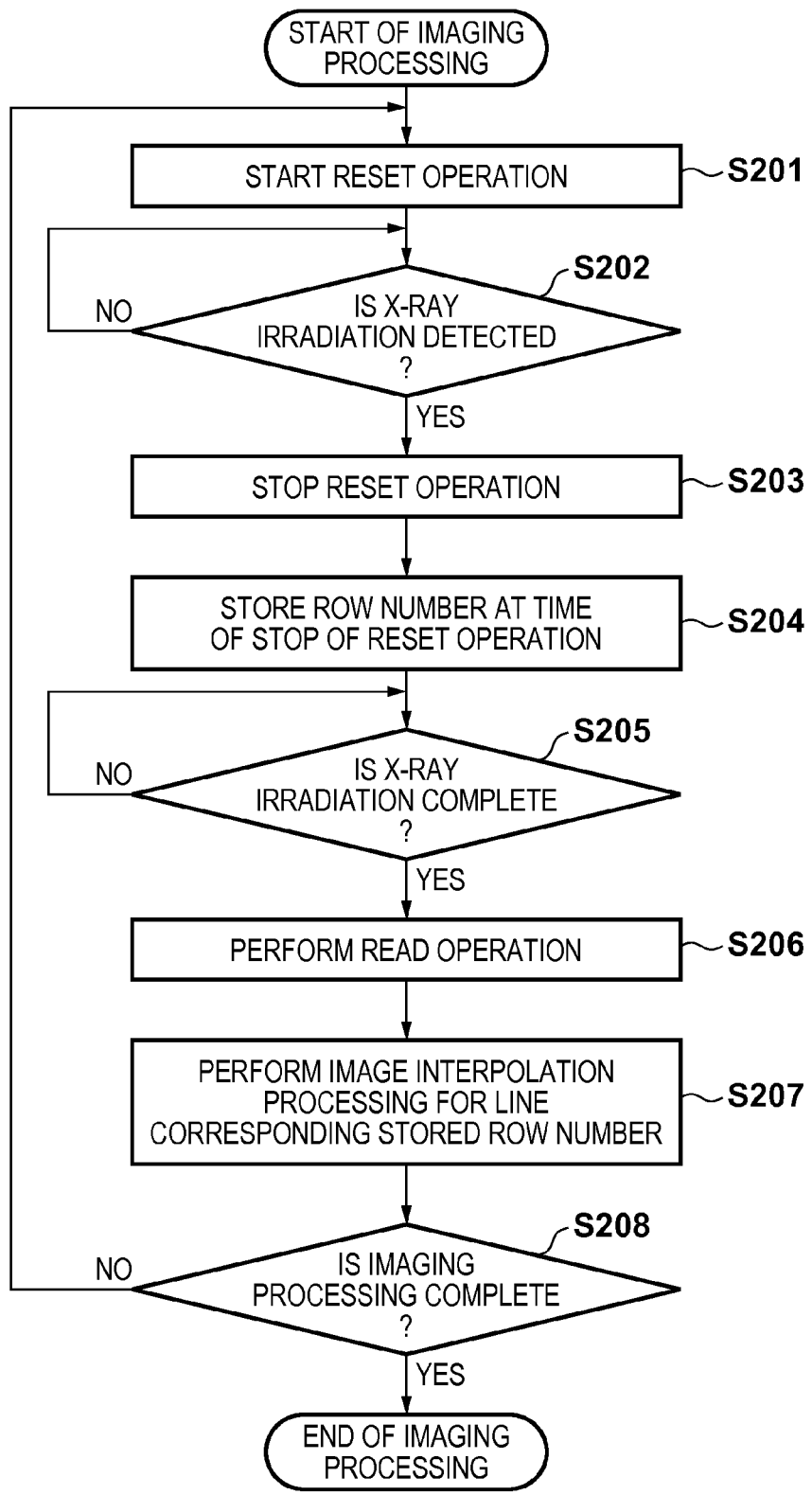
FIG. 2 is a flowchart showing a procedure for imaging processing by the radiation imaging apparatus 100.
Figure 3:
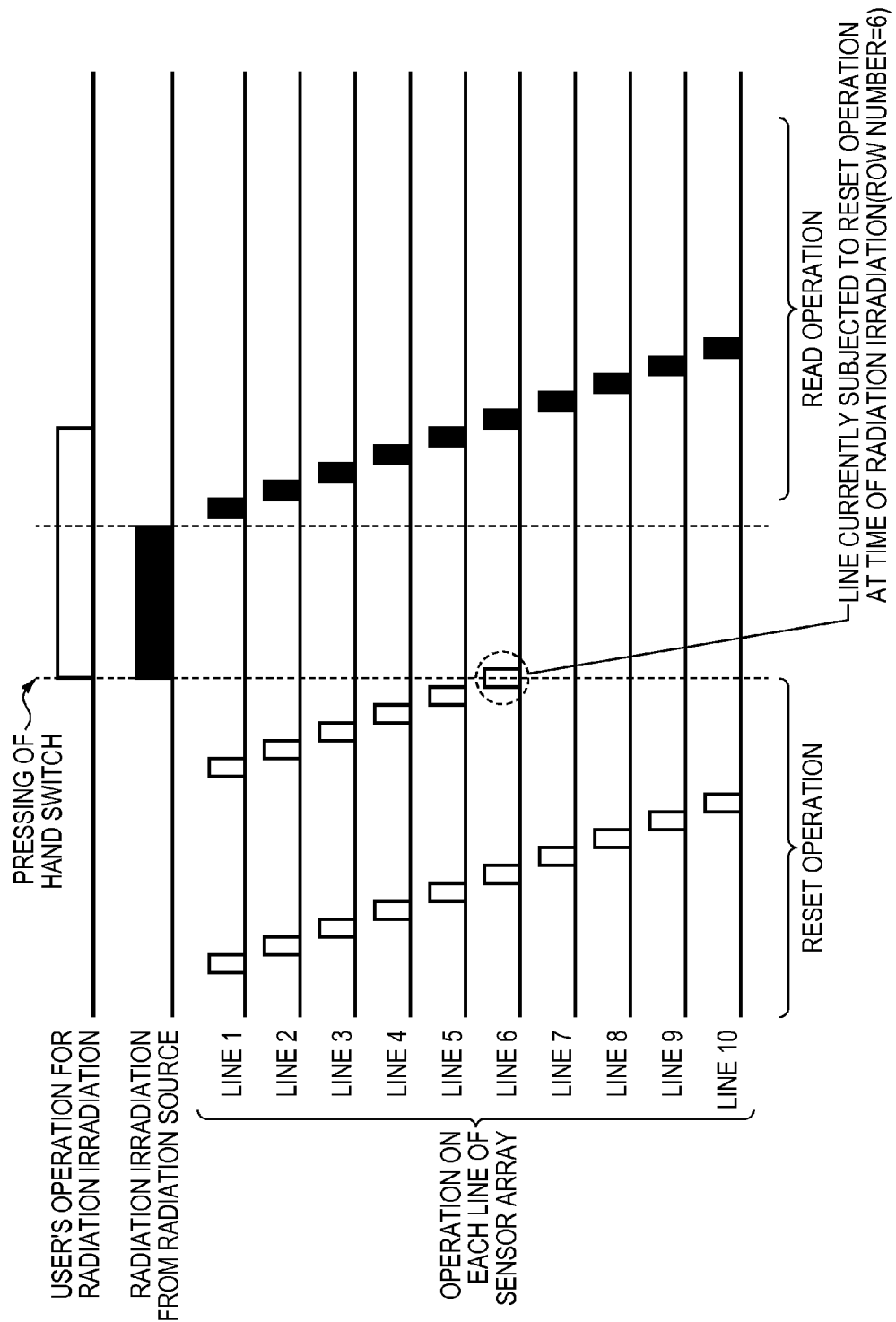
FIG. 3 is a timing chart showing a procedure for imaging processing by the radiation imaging apparatus 100.
Figure 4:
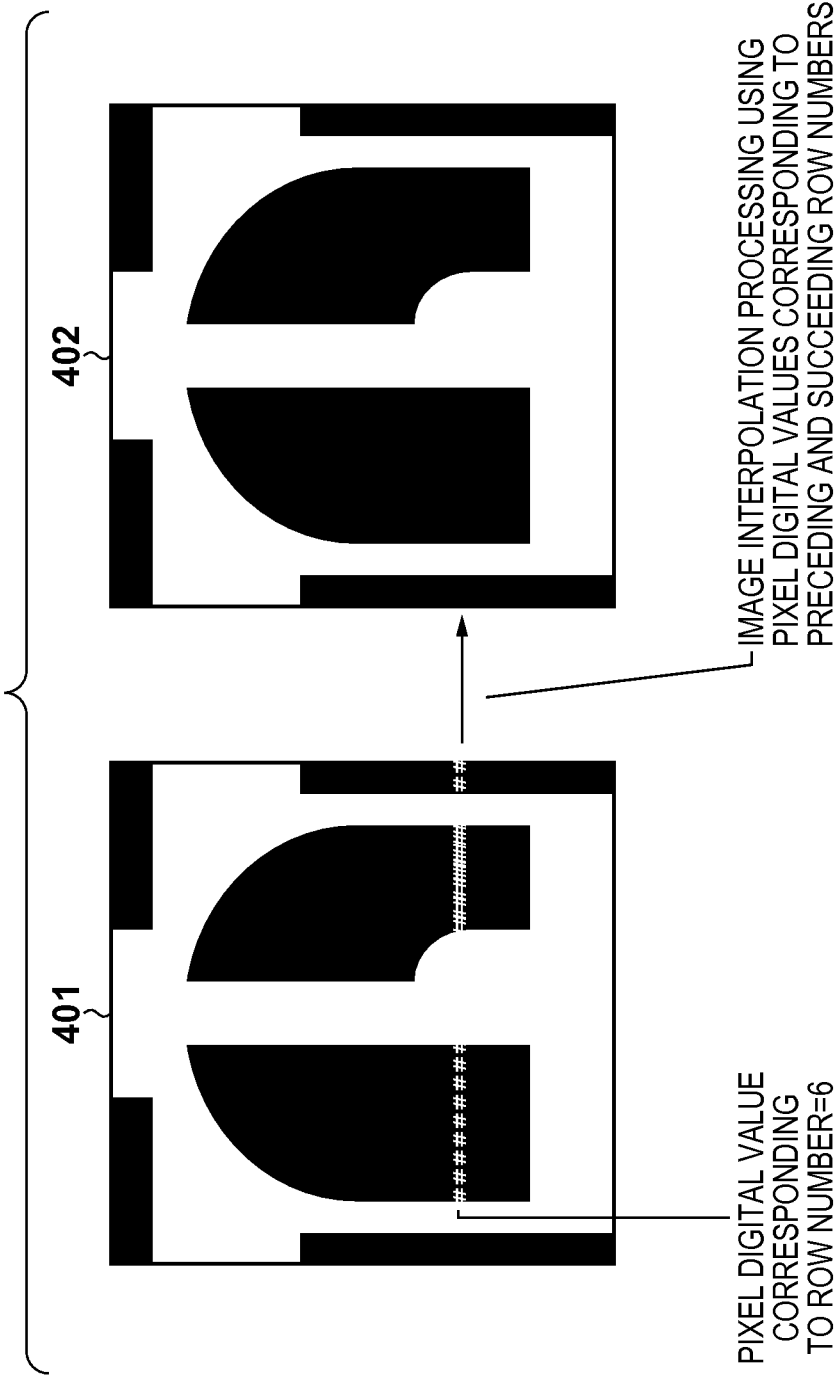
FIG. 4 is a view for explaining image interpolation processing by an image processing circuit 133.

The operation of the radiation imaging apparatus 100 will be described next with reference to FIGS. 2 to 4. FIG. 2 is a flowchart showing a procedure for imaging processing by the radiation imaging apparatus 100. FIG. 3 is a timing chart for the procedure. FIG. 4 is a view for explaining image interpolation processing by the image processing circuit 133.

As shown in FIG. 2, when starting imaging processing, the apparatus starts the reset operation of the two-dimensional sensor array 121 in step S201. When starting reset operation, the apparatus performs the reset operation from the line corresponding to row number=1, as shown in FIG. 3, under the control of the shift register 122. Upon completing the reset operation up to the line corresponding to row number=10, the apparatus performs reset operation again from the line corresponding to row number=1.

During this period, the apparatus determines in step S202 whether the X-ray detector 110 has detected X-ray irradiation. If NO in step S202, the apparatus stands by until X-ray irradiation is detected. If YES in step S202, the process advances to step S203 to stop reset operation.

In step S204, the row number register 132 stores the row number of the line on which reset operation has been executed at the time of stop of reset operation. In step S205, the apparatus determines based on an output from the X-ray detector 110 whether X-ray irradiation is complete. If the apparatus determines that X-ray irradiation is complete, the process advances to step S206.

FIG. 3 exemplifies how the user performs operation to start X-ray irradiation when the apparatus is executing reset operation on the line corresponding to row number=6, and the X-ray source performs X-ray irradiation simultaneously with the operation. As shown in FIG. 3, the radiation imaging apparatus 100 according to this embodiment stops reset operation immediately after the detection of X-ray irradiation, sequentially starts read operation from the line corresponding to row number=1 upon detection of the completion of X-ray irradiation, and stores each pixel digital value in the RAM 140.

In step S207, the apparatus performs image interpolation processing for a value, of the pixel digital values stored in the RAM 140, which concerns the line corresponding to the row number stored in the row number register 132 by using the lines corresponding to the preceding and succeeding row numbers (that is, pixel digital values on the adjacent lines).

Referring to FIG. 4, reference numeral 401 denotes an X-ray image generated based on each pixel digital value stored in the RAM 140. As shown in FIG. 4, the X-ray image 401 lacks in a pixel digital value on the line corresponding to row number=6 because X-ray irradiation is performed during the execution of reset operation on the line. Referring to FIG. 4, reference numeral 402 denotes an X-ray image obtained by performing image interpolation processing for the X-ray image 401 by the image processing circuit 133. As shown in FIG. 4, since the X-ray image 402 is obtained by interpolating the pixel digital value on the line corresponding to row number=6 by the pixel digital values on the preceding and succeeding row numbers (for example, row number=5 and row number=7), it is possible to suppress a deterioration in image quality.

When the image processing circuit 133 completes the above image interpolation processing, the apparatus determines in step S208 whether the imaging processing is complete. If NO in step S208, the process returns to step S201, in which the apparatus starts reset operation again. If the apparatus has received an end instruction from the user and determines to terminate the processing, the apparatus terminates the imaging processing.

As is obvious from the above description, the radiation imaging apparatus 100 according to this embodiment is configured to stop reset operation simultaneously with the detection of X-ray irradiation. This makes it possible to eliminate the delay time between the instant the user performs operation to start X-ray irradiation and the instant radiation is actually irradiated. That is, it is possible to eliminate the time lag between user's operation for radiation irradiation and imaging operation, thereby improving the user-friendliness.

In addition, the radiation imaging apparatus 100 according to this embodiment is configured to store the row number of the line on which reset operation has been executed at the time of stop of the reset operation and interpolate the line corresponding to the stored row number by using the pixel digital values on the lines corresponding to other row numbers. This makes it possible to suppress a deterioration in image quality caused by the deficiency of the pixel digital value on the line corresponding to the above row number.

The radiation imaging apparatus 100 according to this embodiment need not recognize the timing of X-ray irradiation in advance as long as the X-ray detector 110 can detect X-ray irradiation. This makes it unnecessary to perform communication between the X-ray source and the radiation imaging apparatus. This allows free handling of the radiation imaging apparatus, thereby improving the user-friendliness.

Second Embodiment

The first embodiment has exemplified the case in which reset operation is performed line by line. However, the present invention is not limited to this, and can also be applied to a case in which reset operation is simultaneously performed on a plurality of lines (at least some of reset operation timings overlap between a plurality of lines).

When simultaneously performing reset operation on a plurality of lines, if the apparatus is configured to simultaneously perform reset operation on a plurality of lines corresponding to consecutive row numbers, the apparatus cannot make an image processing circuit 133 execute image interpolation processing. For this reason, a radiation imaging apparatus 100 according to this embodiment is configured to distribute a plurality of lines to be simultaneously subjected to reset operation. The operation of the radiation imaging apparatus 100 according to the embodiment will be described in detail below with reference to FIGS. 5 to 9. Note that the following description will be mainly focused on differences from the first embodiment.

Figure 5:
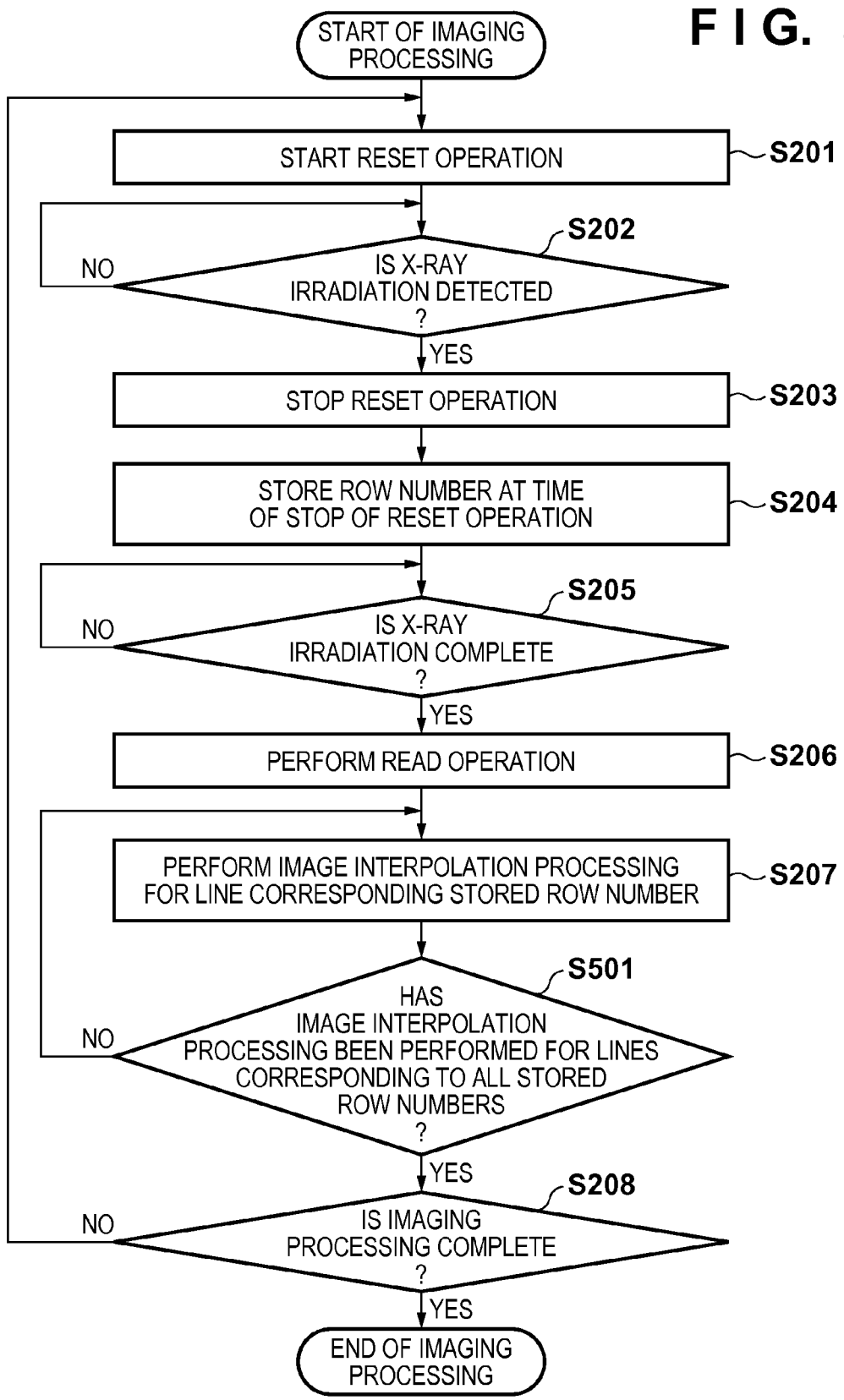
FIG. 5 is a flowchart showing a procedure for imaging processing by the radiation imaging apparatus 100.

FIG. 5 is a flowchart showing a procedure for imaging processing by the radiation imaging apparatus 100 according to this embodiment. FIGS. 6 to 9 are timing charts at the time of imaging processing and views for explaining image interpolation processing. Note that FIGS. 6 and 7 show a case in which the apparatus simultaneously performs reset operation on a plurality of lines corresponding to distributed row numbers. For comparison, FIGS. 8 and 9 show a case in which the apparatus simultaneously performs reset operation on a plurality of lines corresponding to consecutive row numbers.

As shown in FIG. 5, when starting imaging processing, the apparatus starts reset operation on a two-dimensional sensor array 121 in step S201. In this embodiment, when starting reset operation, the apparatus sequentially performs reset operation in the order of row numbers=1, 3, 5, 7, 9, 2, 4, 6, 8, and 10, as shown in FIG. 6, under the control of a shift register 122. At this time, the shift register 122 performs control to simultaneously perform reset operation on lines corresponding to a plurality of row numbers (at least some of reset operation timings overlap between a plurality of lines). Note that the timing chart shown in FIG. 8 shows a case in which the apparatus performs control for reset operation in accordance with an operation sequence, for example, starting from row number=1.

Upon determining in step S202 that X-ray irradiation has been detected, the apparatus stops reset operation in step S203. In step S204, a row number register 132 stores the row numbers of a plurality of lines on which reset operation has been executed at the time of stop of reset operation.

In the case shown in FIG. 6, since the apparatus has performed X-ray irradiation while executing reset operation on the lines corresponding to row numbers=2, 7, and 9, the corresponding row numbers are stored. In the case shown in FIG. 8, since the apparatus has performed X-ray irradiation while executing reset operation on the lines corresponding to row numbers=4, 5, and 6, the corresponding row numbers are stored.

In step S205, the apparatus determines, based on an output from an X-ray detector 110, whether X-ray irradiation has been complete. If the apparatus determines that X-ray irradiation has been complete, the process advances to step S206 to perform read operation.

In the cases shown in FIGS. 6 and 8, the apparatus sequentially performs read operation from row number=1 in accordance with a reset operation sequence. That is, in the case shown in FIG. 6, the apparatus sequentially performs read operation in the order of row numbers=1, 3, 5, 7, 9, 2, 4, 6, 8, and 10, and stores the respective pixel digital values in a RAM 140. In the case shown in FIG. 8, the apparatus sequentially performs read operation in the order of row numbers=1, 2, 3, . . . , 10, and stores the respective pixel digital values in a RAM 140.

In step S207, the apparatus performs image interpolation processing for the line corresponding to the first row number, of the plurality of row numbers stored in the row number register 132, to which the respective pixel digital values stored in the RAM 140 correspond, by using the lines corresponding to the preceding and succeeding row numbers of the first row number.

In step S501, the apparatus determines whether it has executed image interpolation processing for the lines corresponding to all the row numbers stored in the row number register 132. If the apparatus determines in step S501 that the row numbers stored in the row number register 132 include the row number of a line for which image interpolation processing has not yet been executed, the process returns to step S207. If the apparatus determines in step S501 that it has executed image interpolation processing for the lines corresponding to all the row numbers, the process advances to step S208.

Referring to FIG. 7, reference numeral 701 denotes an X-ray image generated based on each pixel digital value stored in the RAM 140. As shown in FIG. 7, the X-ray image 701 lacks in pixel digital values on the lines corresponding to row numbers=2, 7, and 9. Referring to FIG. 7, reference numeral 702 denotes an X-ray image obtained by performing image interpolation processing for the X-ray image 701 in the image processing circuit 133. As shown in FIG. 7, the apparatus interpolates the pixel digital value on the line corresponding to row number=2 by using the pixel digital values on the lines corresponding to the preceding and succeeding row numbers (for example, row number=1 and row number=3 for row number=2), it is possible to suppress a deterioration in the image quality of the X-ray image 702.

Referring to FIG. 9, reference numeral 901 denotes an X-ray image generated based on each pixel digital value stored in the RAM 140. As shown in FIG. 9, the X-ray image 901 lacks in the pixel digital values on the lines corresponding to row numbers=4, 5, and 6. In the case shown in FIG. 9, when the image processing circuit 133 performs image interpolation processing for the X-ray image 901, no pixel digital values may exist at the preceding and succeeding row numbers. For example, with regard to row number=5, since the image lacks in pixel digital values on the lines corresponding to the preceding and succeeding row numbers (row number=4 and row number=6), the apparatus cannot perform image interpolation processing. For this reason, the apparatus cannot improve the image quality of an X-ray image 902 by image interpolation processing. When simultaneously performing reset operation on a plurality of lines, if the apparatus is configured to simultaneously perform reset operation on a plurality of lines corresponding to consecutive row numbers, the image quality deteriorates.

As is obvious from the above description, the radiation imaging apparatus 100 according to this embodiment is configured to simultaneously perform reset operation on a plurality of lines. In addition, the apparatus is configured to distribute a plurality of lines when simultaneously performing reset operation.

This makes it possible to suppress a deterioration in image quality even when simultaneously performing reset operation on a plurality of lines.

Third Embodiment

The first and second embodiments have exemplified the case in which the number of lines of the two-dimensional sensor array is 10. Obviously, however, the present invention is not limited to this and can be equally applied to a two-dimensional sensor array including 11 or more lines.

In the second embodiment, the number of lines to be simultaneously subjected to reset operation is three. However, the present invention is not limited to this. In general, the time for reset operation per line is longer than that for read operation per line. It is therefore preferable to decide the number of lines to be simultaneously subjected to reset operation so as to make the number of lines to be subjected to reset operation per unit time coincide with the number of lines to be subjected to read operation per unit time.

If, for example, the number of lines to be subjected to reset operation per unit time is 1/S (S is an integer) of the number of lines to be subjected to read operation per unit time, it is preferable to decide the number of lines to be simultaneously subjected to reset operation as "S".

In the second embodiment, when distributing a plurality of lines to be simultaneously subjected to reset operation, the reset operation sequence is set to row numbers=1, 3, 5, 7, 9, 2, 4, 6, 8, and 10. That is, the apparatus is configured to perform reset operation, with row numbers increasing by twos (one line skipping). However, the present invention is not limited to this, and may be configured to decide, for example, the number of lines to be skipped in association with the number of lines to be simultaneously subjected to reset operation.

More specifically, letting N (N is an integer) be the number of lines of the two-dimensional sensor array and S be the number of lines to be simultaneously subjected to reset operation, the apparatus may be configured to decide a reset operation sequence such that row numbers increase by n=N/S at a time. In this case, the apparatus performs reset operation every n lines.

Fourth Embodiment

In the first to third embodiments, when starting read operation, the apparatus performs read operation from the line corresponding to row number=1 regardless of the row number stored in the row number register 132. However, the present invention is not limited to this.

For example, the apparatus may be configured to perform read operation from the line corresponding to the row number next to the row number stored in the row number register 132 (the line next to the line on which reset operation has been executed at the start of X-ray irradiation). This is because this arrangement allows keeping of the operation intervals on the respective lines constant in the interval from reset operation to read operation.

The operation of a radiation imaging apparatus 100 according to this embodiment will be described below with reference to FIGS. 10A to 12.

Figure 10A:
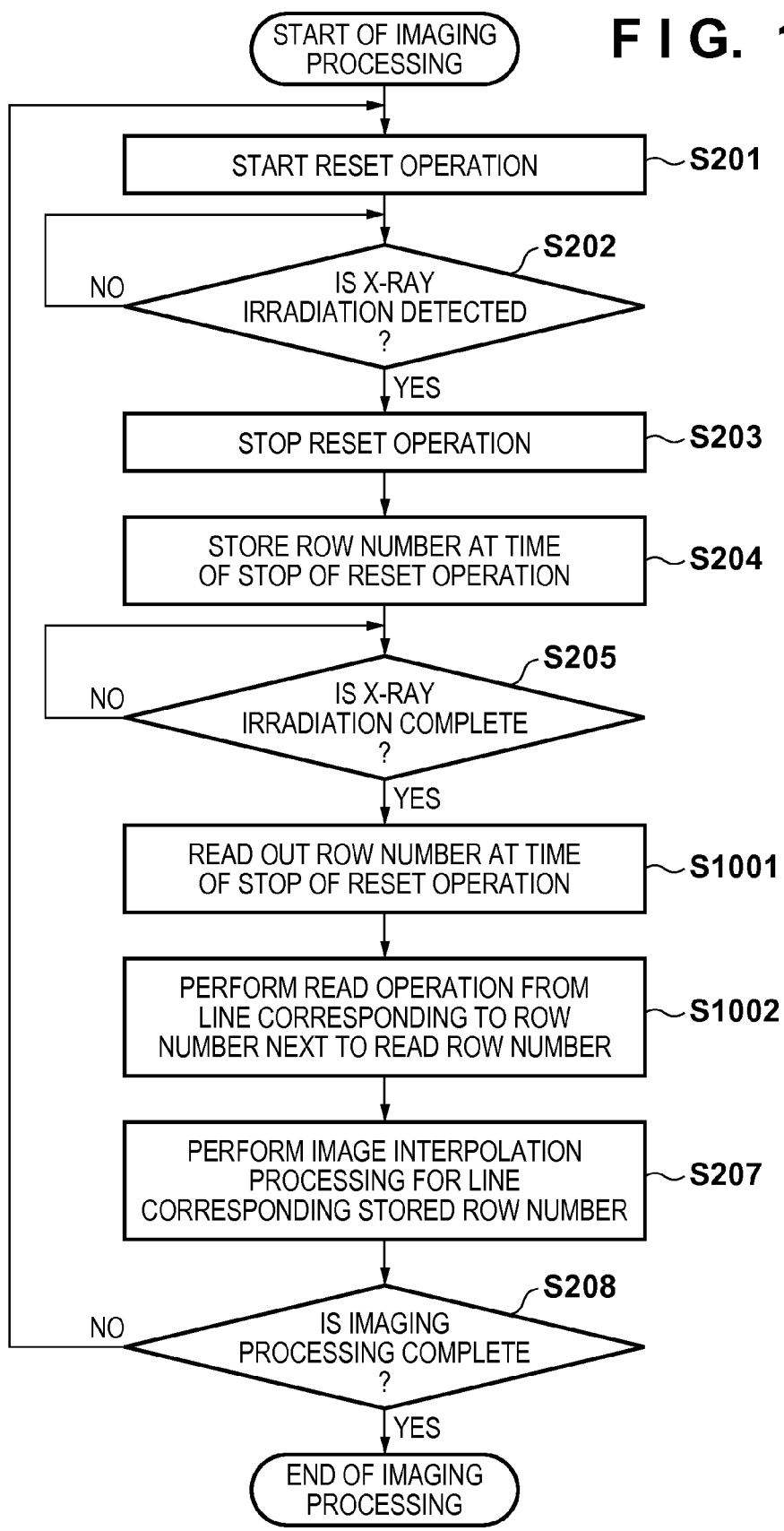
FIG. 10A is a flowchart showing a procedure for imaging processing by the radiation imaging apparatus 100.
Figure 10B:
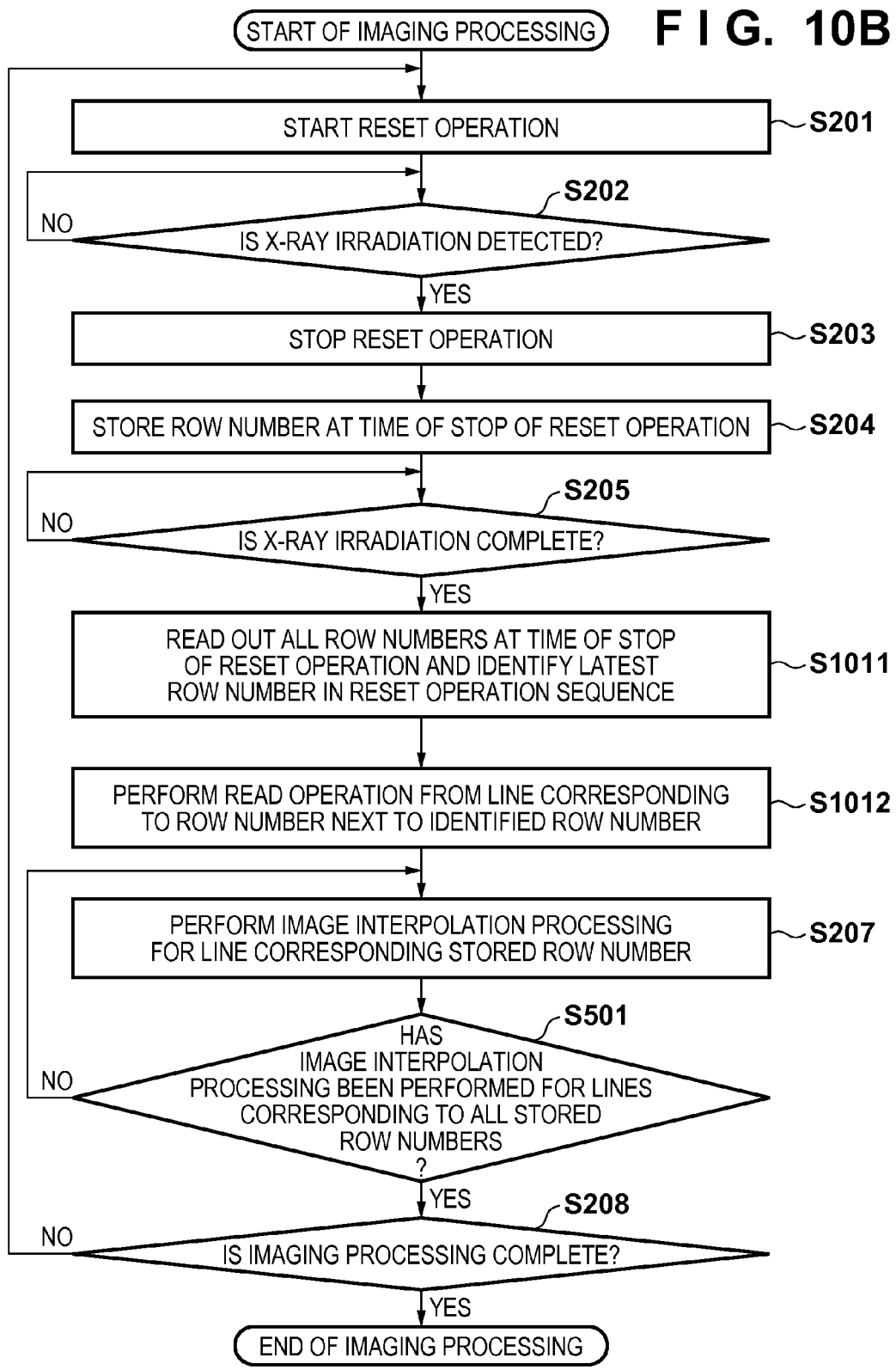
FIG. 10B is a flowchart showing a procedure for imaging processing by the radiation imaging apparatus 100.

FIGS. 10A and 10B are flowcharts showing a procedure for imaging processing by the radiation imaging apparatus 100 according to the fourth embodiment of the present invention. FIG. 11 is a timing chart for a case in which the apparatus executes reset operation for each line. FIG. 12 is a timing chart for a case in which the apparatus collectively executes reset operation for a plurality of lines.

Note that the processing in steps S201 to S205, S207, and S208 in FIG. 10A are the same as those in FIG. 2. The following description will be mainly focused on differences from the processing in FIG. 2.

If the apparatus determines in step S205 that X-ray irradiation is complete, the apparatus reads out the row number stored in the row number register 132 in step S1001. In step S1002, the apparatus performs read operation from the line corresponding to the row number next to the row number read in step S1001.

In the case shown in FIG. 11, since the apparatus has executed X-ray irradiation during execution of reset operation on the line corresponding to row number=6, the apparatus performs read operation from the line corresponding to row number=7 which is the next row number, and stores each pixel digital value in a RAM 140. Setting the line next to the line on which reset operation has been executed during X-ray irradiation as the line from which the apparatus starts read operation in this manner can keep the time intervals from reset operation to read operation on the respective lines constant. In the case shown in FIG. 11, for example, a time interval t1 from reset operation to read operation on the line corresponding to row number=5 is almost equal to a time interval t2 from reset operation to read operation on the line corresponding to row number=7.

Likewise, the processing in steps S201 to S205, S207, S501, and S208 in FIG. 10B is the same as that in FIG. 5, and hence a description of it will be omitted. The following description will be mainly focused on differences from the processing in FIG. 5.

Upon determining in step S205 that the X-ray irradiation is complete, the apparatus reads out all the row numbers stored in the row number register 132 in step S1011. The apparatus then rearranges the read row numbers according to a reset operation sequence and identifies the latest row number in the reset operation sequence.

In the case shown in FIG. 12, the apparatus has performed reset operation in the order of row numbers=1, 4, 7, 10, 3, 6, 9, 2, 5, and 8, and has performed X-ray irradiation during the execution of reset operation on the lines corresponding to row numbers=3, 6, and 10. For this reason, the apparatus rearranges the row numbers of the lines on which reset operation has been executed when X-ray irradiation has been executed into row numbers=10, 3, and 6 according to the reset operation sequence. As a result, the apparatus identifies "6" as the latest row number in the reset operation sequence.

Subsequently, in step S1012, the apparatus starts read operation from the line corresponding to the row number next to the row number identified in step S1011 (the line corresponding to the next row number in the reset operation sequence).

In the case shown in FIG. 12, since the identified row number is "6" and the reset operation sequence corresponds to row numbers=1, 4, 7, 10, 3, 6, 9, 2, 5, and 8, the row number next to the identified row number "6" is "9". The apparatus therefore starts read operation from the line corresponding to row number=9 and performs read operation in the order of row numbers=2, 5, 8, . . . .

When simultaneously performing reset operation on a plurality of lines, the apparatus sets, as the line from which it starts read operation, the line next to the latest line, of the lines on which reset operation has been executed at the time of X-ray irradiation, in the reset operation sequence. This can keep the time intervals from reset operation to read operation on the respective lines constant.

In the case shown in FIG. 12, for example, the time interval t1 from reset operation to read operation on the line corresponding to row number=5 is almost equal to the time interval t2 from reset operation to read operation on the line corresponding to row number=7.

Fifth Embodiment

In each of the first to fourth embodiments, the apparatus is provided with an X-ray detector 110 to detect whether X-rays have been irradiated. The present invention is not limited to this. For example, the apparatus may be configured to detect, based on an output from a two-dimensional sensor array 121 during the execution of reset operation, whether X-rays have been irradiated. This embodiment will be described in detail below.

<1. Arrangement of Radiation Imaging Apparatus>

Figure 13:
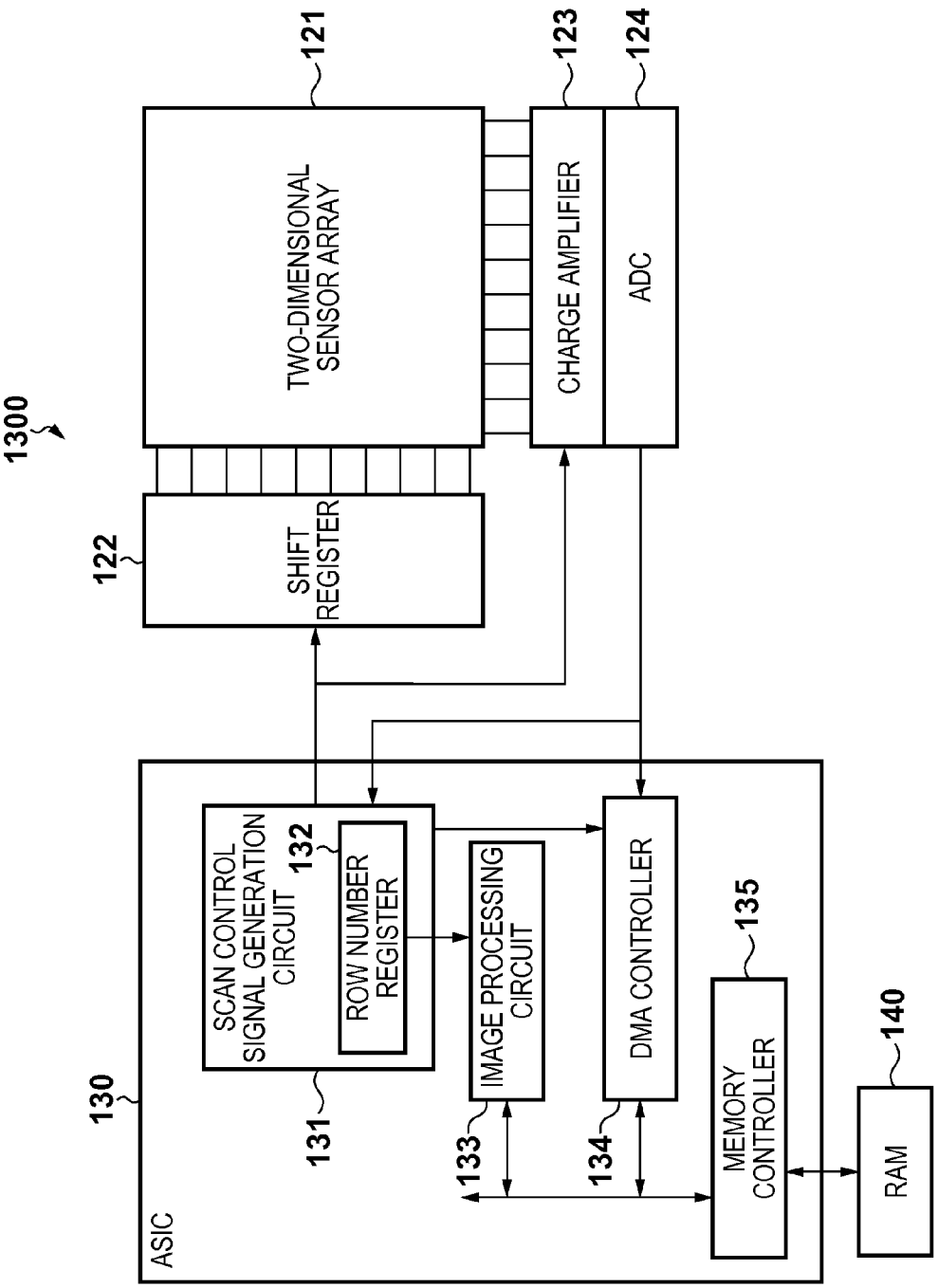
FIG. 13 is a block diagram showing the arrangement of a radiation imaging apparatus 1300.

The arrangement of a radiation imaging apparatus 1300 according to the fifth embodiment of the present invention will be described first. FIG. 13 is a block diagram showing the arrangement of the radiation imaging apparatus 1300 according to the fifth embodiment of the present invention. The following description will be mainly focused on differences from the arrangement in FIG. 1.

The radiation imaging apparatus 1300 shown in FIG. 13 does not include the X-ray detector 110. Instead of this, the apparatus is configured to also transfer an output from an ADC (A/D Converter) 124 to a scan control signal generation circuit 131.

With this arrangement, the scan control signal generation circuit 131 monitors the pixel digital value output from the ADC 124 during the execution of reset operation, and can determine that X-rays have been irradiated, when the pixel digital value abruptly increases. Note that upon determining that X-rays have been irradiated, when the pixel digital value on a line currently subjected to reset operation abruptly increases, the scan control signal generation circuit 131 performs control to continue the reset operation on the line. This makes it possible to determine the completion of X-ray irradiation, when the pixel digital value on the line abruptly decreases afterward.

<2. Operation 1 of Radiation Imaging Apparatus>

Figure 14A:
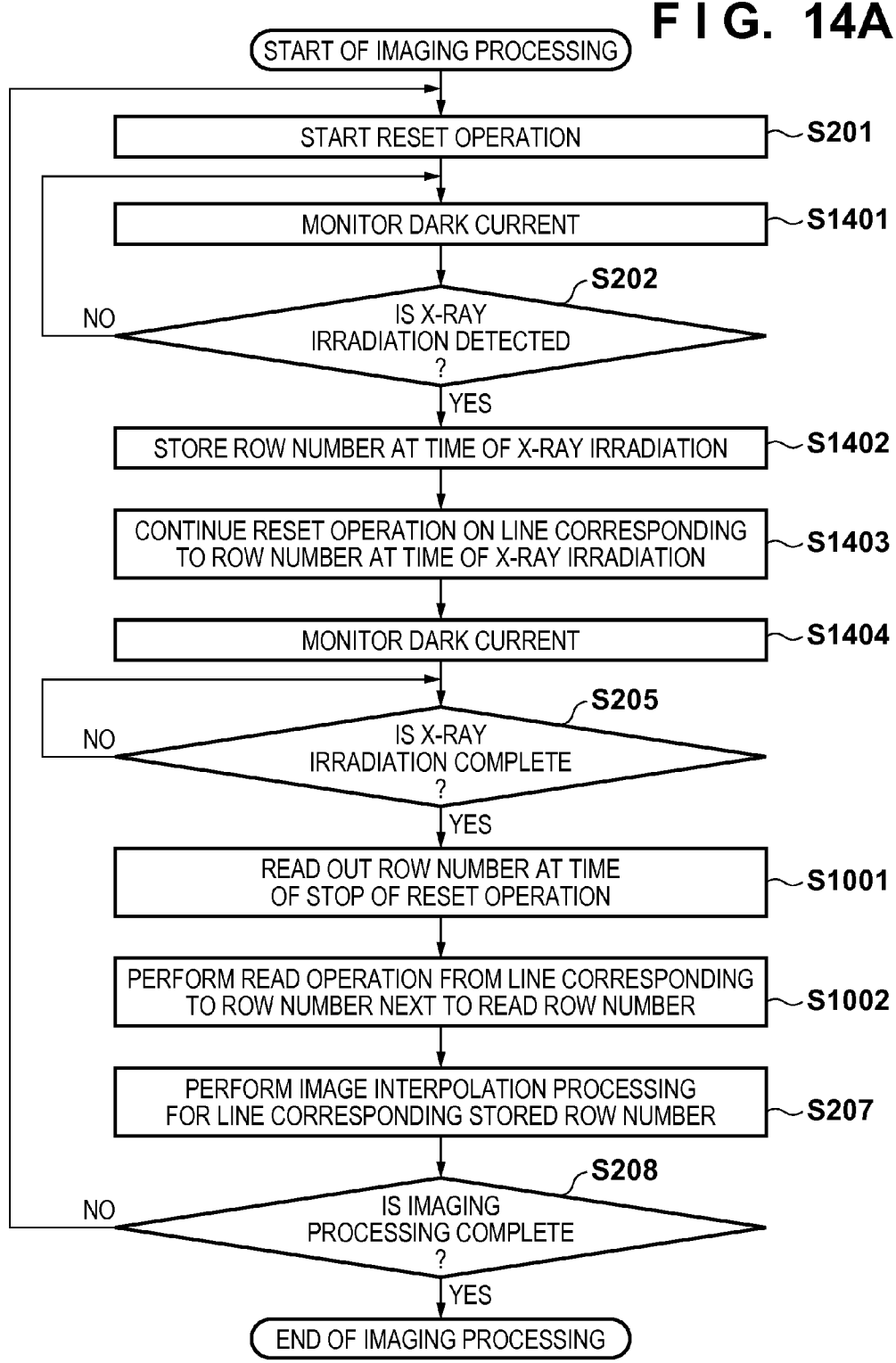
FIG. 14A is a flowchart showing a procedure for imaging processing by the radiation imaging apparatus 1300.

The operation of the radiation imaging apparatus 1300 will be described next with reference to FIGS. 14A and 15. FIG. 14A is a flowchart showing a procedure for imaging processing by the radiation imaging apparatus 1300 which executes reset operation for each line. FIG. 15 is a timing chart for this procedure.

As shown in FIG. 14A, when starting imaging processing, the apparatus starts reset operation for the two-dimensional sensor array 121 in step S201. When starting reset operation, the apparatus sequentially performs reset operation from row number=1, as shown in FIG. 15, under the control of a shift register 122. Upon performing reset operation up to row number=10, the apparatus performs reset operation again from row number=1.

During this period, in step S1401, the scan control signal generation circuit 131 monitors a dark current on each line currently subjected to reset operation. If the scan control signal generation circuit 131 determines in step S1401 that X-rays have been irradiated (YES in step S202), the process advances to step S203. If a dark current has increased to a predetermined threshold or more, the scan control signal generation circuit 131 determines that X-rays have been irradiated. Upon determining that no X-rays have been irradiated, the scan control signal generation circuit 131 continues to monitor a dark current on each line on which reset operation has been performed.

In step S1402, the apparatus stores, in a row number register 132, the row number of a line on which reset operation has been executed upon determining that X-rays have been executed. In step S1403, the apparatus continues reset operation on the line on which reset operation has been executed upon determining that X-rays have been executed without performing reset operation on the next line. This makes the apparatus continue to monitor a dark current on the line in step S1404.

If the apparatus determines the completion of X-ray irradiation (YES in step S205) as a result of monitoring of a dark current in step S1404, the process advances to step S205. When a dark current decreases by a predetermined threshold or more, the scan control signal generation circuit 131 determines that X-ray irradiation is complete.

In the case shown in FIG. 15, when the dark current output from the line corresponding to row number=6 abruptly increases during the execution of reset operation at row number=6 (step S1501), the scan control signal generation circuit 131 determines that X-rays have been irradiated. This makes the scan control signal generation circuit 131 store the row number in the row number register 132, continue reset operation on the line corresponding to the row number, and continue to monitor a dark current.

Upon detecting, as a result of monitoring a dark current, that the dark current output from the line corresponding to row number=6 has abruptly decreased (step S1502), the scan control signal generation circuit 131 determines that X-ray irradiation is complete, and stops reset operation at row number=6 (step S1503).

Since the processing in steps S1001, S1002, S207, and S208 has already been described with reference to FIG. 2 or FIGS. 10A and 10B, a description of it will be omitted hereinafter.

<3. Operation 2 of Radiation Imaging Apparatus>

Another operation of the radiation imaging apparatus 1300 will be described next with reference to FIGS. 14B and 16. FIG. 14B is a flowchart showing a procedure for imaging processing by the radiation imaging apparatus 1300 which collectively executes reset operation on a plurality of lines. FIG. 16 is a timing chart for this procedure.

As shown in FIG. 14B, when starting imaging processing, the apparatus starts reset operation for the two-dimensional sensor array 121 in step S201. When starting reset operation, the apparatus sequentially performs reset operation in the order of row numbers=1, 4, 7, 10, 3, 6, 9, 2, 5, and 8, as shown in FIG. 16, under the control of the shift register 122.

During this period, in step S1411, the scan control signal generation circuit 131 monitors a dark current on each line currently subjected to reset operation. If the scan control signal generation circuit 131 determines in step S1411 that X-rays have been irradiated (YES in step S202), the process advances to step S203. If a dark current has increased to a predetermined threshold or more, the scan control signal generation circuit 131 determines that X-rays have been irradiated. Upon determining that no X-rays have been irradiated, the scan control signal generation circuit 131 continues to monitor a dark current on each line on which reset operation has been performed.

In step S1412, the apparatus stores, in the row number register 132, the row numbers of all the lines on which reset operation has been executed upon determining that X-rays have been executed. In step S1413, the apparatus continues reset operation on all the lines on which reset operation has been executed upon determining that X-rays have been executed without performing reset operation on the next line. This makes the apparatus continue to monitor dark currents on the plurality of lines in step S1414.

If the apparatus determines the completion of X-ray irradiation (YES in step S205) as a result of monitoring of dark currents in step S1414, the process advances to step S205. When a dark current on each line decreases by a predetermined threshold or more, the scan control signal generation circuit 131 determines that X-ray irradiation is complete.

In the case shown in FIG. 16, when the dark currents output from the lines corresponding to row numbers=3, 6, and 10 abruptly increase during the execution of reset operation at row numbers=3, 6, and (step S1601), the scan control signal generation circuit 131 determines that X-rays have been irradiated. This makes the scan control signal generation circuit 131 store the row numbers in the row number register 132, continue reset operation on the lines corresponding to the row numbers, and continue to monitor dark currents.

Upon detecting, as a result of monitoring dark currents, that the dark currents output from the lines corresponding to row numbers=3, 6, and 10 have abruptly decreased (step S1602), the scan control signal generation circuit 131 determines that X-ray irradiation is complete, and stops reset operation at row numbers=3, 6, 10 (steps S1603 to S1605).

Since the processing in steps S1011, S1012, S207, S501, and S208 has already been described with reference to FIG. 2, FIG. 5, and FIGS. 10A and 10B, a description of it will be omitted hereinafter.

As is obvious from the above description, the radiation imaging apparatus 1300 according to this embodiment is configured to monitor dark currents on lines currently subjected to reset operation and detect the execution of X-ray irradiation based on changes in dark currents, instead of being provided with an X-ray detector. This apparatus is further configured to continue reset operation on lines subjected to reset operation when determining that X-rays have been irradiated and monitor the completion of X-ray irradiation.

As a result, it is possible to obtain the same effects as those of the first to fourth embodiments without using any X-ray detector.

Sixth Embodiment

The fifth embodiment is configured to monitor outputs from the ADC 124 to detect the execution of X-ray irradiation, instead of being provided with the X-ray detector 110. However, the present invention is not limited to this. For example, the apparatus may be configured to include a printed board capable of converting a current on a sensor bias line of the two-dimensional sensor array 121 into a voltage and outputting it as a digital value and monitor digital values output from the printed board (changes in the state of the two-dimensional sensor array 121).

The fifth embodiment described above is configured to determine that X-rays have been irradiated, if a pixel digital value has abruptly increased. However, the present invention is not limited to this. For example, this apparatus may be configured to store a pixel digital value in a state in which no X-rays are irradiated and determine whether X-ray irradiation has been performed, by comparison with the stored pixel digital value.

Figure 17:
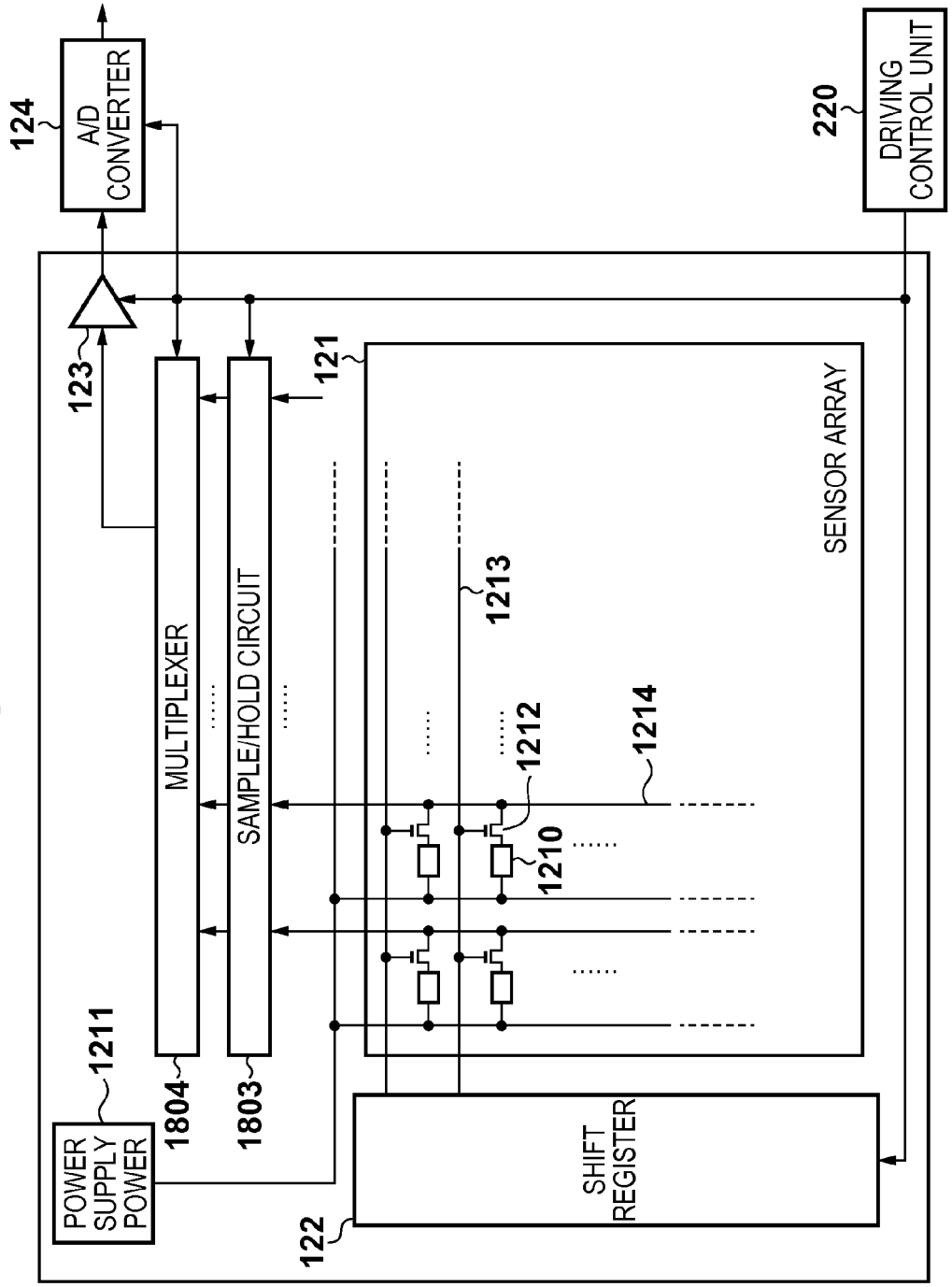
FIG. 17 is a view showing the arrangement of a two-dimensional sensor array and its peripheral circuit.

FIG. 17 shows the arrangement of the two-dimensional sensor array 121 according to this embodiment and its peripheral circuit. The two-dimensional sensor array 121 includes a plurality of photoelectric conversion elements 1210 arranged in a matrix form and TFTs (Thin Film Transistors) 1212 respectively coupled to the photoelectric conversion elements 1210. A power supply 1211 applies a bias voltage via a bias line connected to each photoelectric conversion element 1210. The voltage applied to a gate line 1213 commonly provided for each row of the TFTs 1212 controls conduction of each TFT 1212. Each gate line 1213 is connected to the output side of a shift register 122 operating as a driving circuit, and receives an output from the shift register 122 to control ON/OFF operation of each TFT 1212 on a row basis. The gate lines 1213 respectively correspond to LINE 1 to LINE 10 in FIGS. 3, 6, 8, 11, 12, 15, 16, 17, 20, 21, and 22. When the TFT 1212 is turned on, the charge stored in the photoelectric conversion element 1210 is output via a signal line 1214. A sample/hold circuit 1803 then holds it as an electrical signal.

The photoelectric conversion elements 1210 of the two-dimensional sensor array 121 may be so-called direct type elements which convert X-rays into charges or may be elements which generate charges upon receiving visible light. In this case, a phosphor which converts X-rays into visible light is stacked on the two-dimensional sensor array 121.

The shift register 122 simultaneously addresses all the pixels on a given row on the two-dimensional sensor array 121. The sample/hold circuit 1803 then holds charges from the respective pixels on the row. The held charges output from the pixels are sequentially read via a multiplexer 1804. A charge amplifier 123 amplifies the charges. An A/D converter 143 then converts the charges into digital values. Every time scanning on each row is complete, the shift register 122 sequentially drives the next row on the sensor array. Finally, the charges output from all the pixels are converted into digital values. This makes it possible to read out radiation image data. In this case, the apparatus scans while fixing the voltage applied to each column signal line to a specific value and discards acquired charges, thereby discharging dark charges and performing scanning for the initialization of the sensor. A driving control unit 220 including a scan control signal generation circuit 131 of an ASIC 130 performs control such as driving and read operation of the sensor unit.

The image data converted into digital values allows obtaining of a captured image from which unnecessary dark charge components are removed by performing the offset correction of subtracting the offset image data acquired from only the dark charge components without radiation irradiation from radiation image data.

Figure 18:
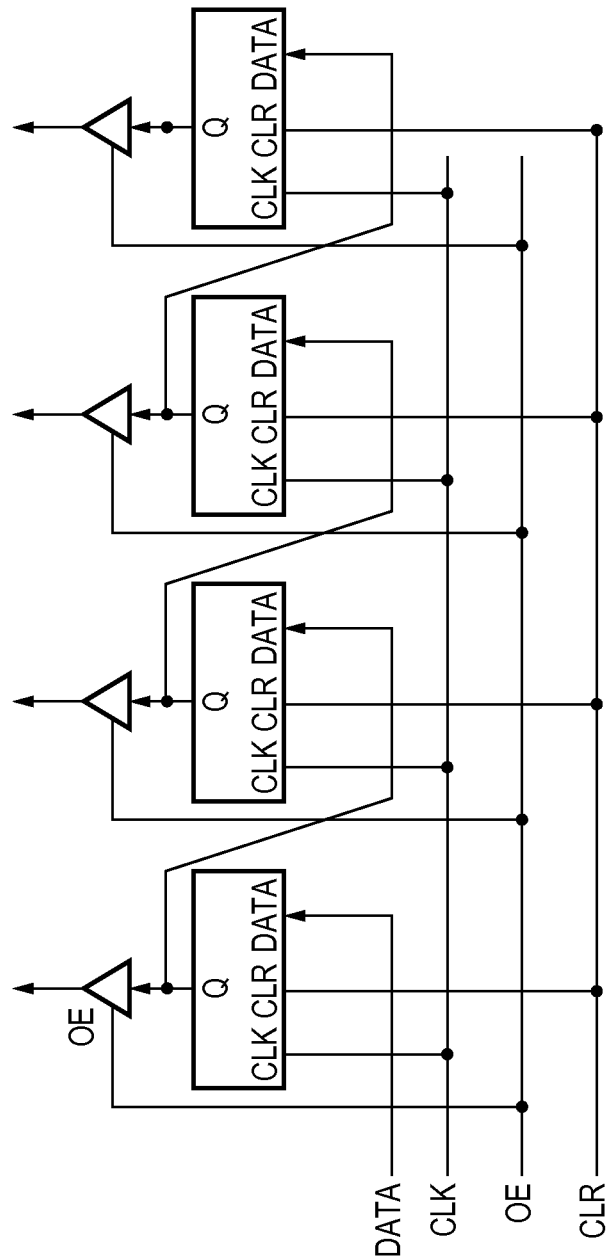
FIG. 18 is a view showing an example of the structure of a shift register 122.

FIG. 18 shows an example of the structure of the shift register 122 according to the above embodiment. The shift register 122 includes a plurality of registers and AND gates connected to the output sides of the registers. The output sides of the respective registers are connected to the DATA pins on the input sides of the registers adjacent to each other in a predetermined direction. The shift register 122 includes a DATA pin which inputs data to the first register, a CLK pin which instructs all the registers to capture next data, an OE pin which simultaneously permits/inhibits outputs from all the registers, and a CLR pin which simultaneously clears the stored contents of all the registers. The CLK and CLR pins are connected to the CLK and CLR input portions of the respective registers. The DATA pin is connected to the DATA input portion of the first register. The DATA input portion of each succeeding register is connected to the output portion of the immediately preceding register. The OE pin is connected to the AND gates connected to the respective registers. With this arrangement, the respective inputs to the CLK, CLR, and OE pins directly control the state of all the registers or AND gates. Each input to the DATA pin directly controls only the state of the first register. The scan control signal generation circuit 131 included in the driving control unit 220 generates control signal inputs for the respective pins. An output from each AND gate is a digital value representing 0 or 1. Voltages indicating such data values are connected as the outputs of the shift register to the respective gate lines 1213. Alternatively, amplification units provided for the respective AND gates perform predetermined amplification of voltages indicating the respective digital values and output the amplified voltages. These output voltages include the first voltage which corresponds to digital value "1" and turns on the TFT 1212 and the second voltage which digital value "0" and turns off the TFT 1212.

Each register receives an input from the DATA pin and stores either the first data for turning on the TFTs 1212 on a corresponding row of the two-dimensional sensor array 121 or the second data for turning off them. Controlling the CLK pin causes each register to capture the stored content of the adjacent register. That is, inputting one clock pulse to the CLK pin can shift the selected state of each row of the TFTs 1212 by one row. Using the DATA and CLK pins in combination can select an arbitrary combination of rows of the two-dimensional sensor array 121. In addition, setting the OE pin in the OFF state can fix the output of the register to the OFF state regardless of the stored content. This can prevent any row of the two-dimensional sensor array 121 from being unintentionally selected during shift operation.

A method of controlling the shift register 122 for the implementation of reset scanning in FIG. 12 will be described with reference to FIG. 19. As described above, the selected state of each row is changed by inputting a clock pulse to the CLK pin. Since the skip count is three, clock pulses are input for every three rows to shift the selected state. The OE pin is switched to the OFF state so as not to select any row which should not be selected during this shift operation. If a selected row is added near the head of the two-dimensional sensor array 121 as the scan progresses, the DATA pin is controlled to satisfy this. Upon completion of the shift operation, the OE pin is switched to the ON state to select a row of the two-dimensional sensor array 121.

As described above, one selection of each row in FIG. 12 is actually implemented by a plurality of intermittent selections (three times of ON switching and OFF switching in this case). However, since the duration of shift operation is sufficiently shorter than a selection period, a plurality of times of selection can be regarded as continuous operation.

The driving operation shown in FIG. 12 is executed in this manner. In the above case, TFTs are sequentially tuned on with a skip count of three, that is, for every two rows. However, the present invention is not limited to this. Changing the skip count will implement the driving operation of sequentially turning on TFTs for every m ($\geq 1$) rows. In addition to reset scanning, the same operation is implemented in subsequent read scanning.

A radiation imaging apparatus according to another embodiment of the present invention will be described. This apparatus has the same structure as that in the above embodiment, and differs from it only in the method of scanning the two-dimensional sensor array 121. Therefore, only this point will be described.

In the first and second embodiments, every time the selected state of a row is switched, the selection of one row is canceled, and one row is additionally selected. However, this operation is not essential to the present invention. A plurality of rows may be subjected to selection cancellation and addition per switching operation or all selected rows may be simultaneously subjected to selection cancellation and addition.

This embodiment is configured to control the two-dimensional sensor array 121 in consideration of this point. FIG. 20 shows the corresponding operation. In the embodiment, skip count I=3 is set. The embodiment differs from the second embodiment in that all simultaneously selected rows are simultaneously subjected to selection cancellation and addition. Since reset periods are uniformly distributed on each row, the number of rows simultaneous selected at each moment in scanning varies in the range of 3 or 4. However, both the embodiments have the common feature that rows to be simultaneously selected are not adjacent to each other. In reset scanning, selection of a plurality of rows is simultaneously started and ended. In contrast, in read scanning, rows are selected one by one, and hence the periods during which dark currents are accumulated on the respective rows are not equal in a strict sense. However, it is possible to make a great improvement as compared with the differences between accumulation periods in FIG. 2.

FIG. 21 shows control on the shift register 122, which implements scanning in this embodiment. At an early stage in scanning, in order to simultaneously start selecting a plurality of rows, many clocks and data are input to the shift register 122 to turn on a plurality of registers, thereby setting an initial state. At this time, the state of skip count I=3 is implemented in the shift register 122. Controlling the OE pin in this state will simultaneously ON/OFF-control the TFTs on a plurality of rows. Since the skip selection state has already been set in the shift register 122, clock pulses for carrying on scanning may be input one by one to shift selected rows one by one. Only when the leading row is selected again as the scan progresses, a new ON signal is input to the DATA pin when inputting a clock.

Another radiation irradiation detection method can detect radiation irradiation by connecting, to a bias line connected to a power supply 1211, a current measurement unit which monitors a current flowing on the bias line. When radiation is irradiated, the charge accumulated in a photoelectric conversion elements 1210 in reset scanning is output via a signal line 1214, and charge flows on the bias line so as to compensate for the output of the charge. Therefore, radiation irradiation is detected by detecting a current on this bias line. The current measurement unit is configured such that a resistor and an operational amplifier are connected in parallel, the bias line is connected to the input portion of the operational amplifier, and an amplification unit and an ADC are connected to the output portion of the operational amplifier. The resistor performs DC voltage conversion. The amplification unit amplifies this voltage. The ADC converts the voltage into a digital value. The digital value is input to an FPGA operating as a comparator and is compared with a first digital threshold a in the FPGA. The FPGA periodically samples this voltage. When the voltage becomes larger than the first digital threshold a, the FPGA determines that radiation irradiation has started.

Likewise, in combination with the driving operations shown in FIGS. 15 and 16, it is also possible to determine the end of radiation irradiation. When determining the end of irradiation, after determining that radiation irradiation has started, the FPGA determines that radiation irradiation has ended, when the voltage sampled by the FPGA becomes smaller than a second digital threshold b.

The above-described embodiment of the present invention can improve the user-friendliness of a radiation imaging apparatus configured to perform the reset operation of a sensor array.

Other Embodiments

Embodiments of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable medium).

While the embodiments of the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Applications No. 2012-128403 filed Jun. 5, 2012, and No. 2013-052433, filed Mar. 14, 2013, which are hereby incorporated by reference herein in their entirety.

What is claimed is:

1. An X-ray radiation imaging apparatus including a sensor array including a plurality of pixels arranged in a matrix form, a switch element connected to each pixel, and a column signal line common to pixels on each column to which each pixel is connected via the switch element, the X-ray radiation imaging apparatus comprising:
   a first control unit configured to control reset operation of sequentially removing signals respectively output from a plurality of lines constituting the sensor array;
   an identifying unit configured to identify a line currently subjected to the reset operation when a start of X-ray radiation irradiation is detected;
   a second control unit configured to control read operation of reading a signal output from each of the plurality of lines at a timing set in advance for each line upon completion of the X-ray radiation irradiation;
   an interpolation unit configured to interpolate an image, which is part of an image generated based on signals read by the read operation, and which corresponds to a line identified by the identifying unit, by using images of adjacent lines;
   a driving circuit which performs control to set the switch element in an ON state and an OFF state for each row; and
   a detection unit configured to detect X-ray radiation irradiation by monitoring an electrical signal output from the pixel,
   wherein the first control unit controls the driving circuit to set a switch element on each row in an ON state for a predetermined period,
   wherein, with a first row, a second row, a third row, and a fourth row arranged in the order named, the first control unit performs control to set switch elements on the first and third rows in an ON state while setting switch elements on the second and fourth rows in an OFF state in a first period and to set switch elements on the second and fourth rows in an ON state while setting the switch elements on the first and third rows in an OFF state in a second period which does not overlap the first period, and wherein the first control unit causes the switch element on a row which is in an ON state when the detection circuit has detected X-ray radiation irradiation to continue an ON state for a period longer than the predetermined period.

2. The apparatus according to claim 1, wherein the first control unit controls a timing of removal of a signal output from each of the plurality of lines so as to perform the reset operation for every n lines (n being an integer ≥2).

3. The apparatus according to claim 2, wherein the first control unit controls the timing so as to satisfy a relation n=N/S where S (S being an integer ≥2) is the number of lines on which timings of the reset operation overlap and N is the number of lines constituting the sensor array (and N being an integer ≥2).

4. The apparatus according to claim 1, wherein the second control unit performs control to start the read operation from a line next to the line identified by the identifying unit.

5. The apparatus according to claim 4, wherein the second control unit performs control to start the read operation from a line next to a latest line in a sequence of the reset operation when the identifying unit identifies a plurality of lines.

6. The apparatus according to claim 1, wherein the identifying unit identifies a line currently subjected to the reset operation when the detection unit detects the X-ray radiation irradiation.

7. The apparatus according to claim 6, wherein the detection unit detects the X-ray radiation irradiation based on a change in a state of the sensor array.

8. The apparatus according to claim 1, further comprising a monitoring unit configured to monitor a signal output from each line in the reset operation, wherein the identifying unit identifies a line currently subjected to the reset operation when it is determined, based on a change in the signal monitored by the monitoring unit, that the X-ray radiation has been irradiated.

9. The apparatus according to claim 8, wherein the second control unit starts the read operation when it is determined, based on a change in the signal monitored by the monitoring unit, that the X-ray radiation irradiation is complete.

10. The apparatus according to claim 1, wherein the first control unit causes the driving circuit to set a switch element on each row in an ON state for a predetermined period so as to simultaneously set the switch elements on a plurality of rows in an ON state while inhibiting the switch elements on adjacent rows from being simultaneously set in an ON state.

11. The apparatus according to claim 1, wherein the first control unit performs control to sequentially set the switch elements on every $m^{th}$ row (m being ≥1), for every predetermined number of switch elements.

12. The apparatus according to claim 1, wherein the first control unit sequentially performs control to sequentially set the switch elements on odd-numbered rows in an ON state, for every predetermined number of switch elements, and control to sequentially set the switch elements on even-numbered rows in an ON state, for every predetermined number of switch elements.

13. The apparatus according to claim 1, further comprising a specifying unit configured to specify a number of a row which is in an ON state when the detection circuit has detected X-ray radiation irradiation.

14. The apparatus according to claim 13, further comprising a correction unit configured to correct image data corresponding to at least the specified row based on image data corresponding to rows adjacent to the specified row.

15. The apparatus according to claim 1, wherein the detection circuit further detects an end of X-ray radiation irradiation based on an electrical signal from a row corresponding to the switch element caused to continue the ON state.

16. The apparatus according to claim 15, wherein the first control unit shifts the switch element on the row which is caused to continue the ON state to an OFF state when an end of the X-ray radiation irradiation is detected.

17. The apparatus according to claim 1, further comprising a reading circuit which reads an electrical signal output from each pixel to the column signal line when a switch element on the each row is set in an ON state, wherein the first control unit obtains image data by causing the reading circuit to read electrical signals obtained by setting switch elements on the each row in an OFF state in accordance with detection of X-ray radiation irradiation by the detection circuit and sequentially setting switch elements on the each row in an ON state after a lapse of a predetermined period.

18. The apparatus according to claim 17, wherein the first control unit terminates an ON state of the switch element on the row which is in an ON state when the detection circuit has detected X-ray radiation irradiation in accordance with detection of the X-ray radiation irradiation even before the lapse of the predetermined period.

19. The apparatus according to claim 17, wherein the first control unit performs control such that the predetermined period, during which the switch element is in ON state before detection of X-ray radiation by the detection circuit, is longer than a period during which the switch element is in an ON state when the image data is obtained.

20. The apparatus according to claim 1, wherein the first control unit sequentially shifts switch elements on each row to an ON state such that a period during which a given row is in an ON state overlaps a period during which another row is in an ON state for a period shorter than the period during which the given row is in an ON state.

21. The apparatus according to claim 1, wherein the driving circuit sets a switch element on the first row in an OFF state for a predetermined period between a first period overlapping a period, of a period during which a switch element on the first row is in an ON state, during which a switch element on the third row is in an ON state, and a second period which does not overlap a period, of the period during which the switch element on the first row is in an ON state, during which the switch element on the third row is in an ON state.

22. A method of controlling an X-ray radiation imaging apparatus including a sensor array including a plurality of pixels arranged in a matrix form, a switch element connected to each pixel, and a column signal line common to pixels on each column to which each pixel is connected via the switch element, and a driving circuit which performs control to set the switch element in an ON state and an OFF state for each row, and a detection unit configured to detect X-ray radiation irradiation by monitoring an electrical signal output from the pixel, the method comprising:

a first control step of controlling reset operation of sequentially removing signals respectively output from a plurality of lines constituting the sensor array;

an identifying step of identifying a line currently subjected to the reset operation when a start of X-ray radiation irradiation is detected;

a second control step of controlling read operation of reading a signal output from each of the plurality of lines at a timing set in advance for each line upon completion of the X-ray radiation irradiation; and an interpolation step of interpolating an image, which is part of an image generated based on signals read by the read operation, and which corresponds to a line identified in the identifying step, by using images of adjacent lines, wherein, in the first control step, control of the driving circuit is executed to set a switch element on each row in an ON state for a predetermined period, wherein with a first row, a second row, a third row, and a fourth row arranged in the order named, in the first control step, control is executed to set switch elements on the first and third rows in an ON state while setting switch elements on the second and fourth rows in an OFF state in a first period and to set the switch elements on the second and fourth rows in an ON state while setting the switch elements on the first and third rows in an OFF state in a second period which does not overlap the first period, and wherein in the first control step, the switch element on a row which is in an ON state when the detection circuit has detected X-ray radiation irradiation is caused to continue the ON state for a period longer than the predetermined period.

23. A non-transitory computer-readable storage medium storing a program for causing a computer to execute steps in a method of controlling an X-ray radiation imaging apparatus including a sensor array including a plurality of pixels arranged in a matrix form, a switch element connected to each pixel, and a column signal line common to pixels on each column to which each pixel is connected via the switch element, and a driving circuit which performs control to set the switch element in an ON state and an OFF state for each row, and a detection unit configured to detect X-ray radiation irradiation by monitoring an electrical signal output from the pixel, the method comprising:

a first control step of controlling reset operation of sequentially removing signals respectively output from a plurality of lines constituting the sensor array;

an identifying step of identifying a line currently subjected to the reset operation when a start of X-ray radiation irradiation is detected;

a second control step of controlling read operation of reading a signal output from each of the plurality of lines at a timing set in advance for each line upon completion of the X-ray radiation irradiation; and an interpolation step of interpolating an image, which is part of an image generated based on signals read by the read operation, and which corresponds to a line identified in the identifying step, by using images of adjacent lines, wherein, in the first control step, control of the driving circuit is executed to set a switch element on each row in an ON state for a predetermined period, wherein with a first row, a second row, a third row, and a fourth row arranged in the order named, in the first control step, control is executed to set switch elements on the first and third rows in an ON state while setting switch elements on the second and fourth rows in an OFF state in a first period and to set the switch elements on the second and fourth rows in an ON state while setting the switch elements on the first and third rows in an OFF state in a second period which does not overlap the first period, and wherein in the first control step, the switch element on a row which is in an ON state when the detection circuit has detected X-ray radiation irradiation is caused to continue the ON state for a period longer than the predetermined period.

24. An X-ray radiation imaging apparatus comprising:

an imaging unit including a plurality of pixels arranged in a matrix form, a switch element connected to each pixel, and a column signal line common to pixels on each column to which each pixel is connected via the switch element;

a driving circuit which performs control to set the switch element in an ON state and an OFF state for each row;

a control unit which causes the driving circuit to set a switch element on each row in an ON state for a predetermined period so as to simultaneously set the switch elements on a plurality of rows in an ON state while inhibiting the switch elements on adjacent rows from being simultaneously set in an ON state; and a detection circuit which detects X-ray radiation irradiation by monitoring an electrical signal output from the pixel by the control, wherein the control unit causes the switch element on a row which is in an ON state when the detection circuit has detected X-ray radiation irradiation to continue an ON state for a period longer than the predetermined period.

25. An X-ray radiation imaging apparatus comprising:

an imaging unit including a plurality of pixels arranged in a matrix form, a switch element connected to each pixel, and a column signal line common to pixels on each column to which each pixel is connected via the switch element;

a driving circuit which performs control to set the switch element in an ON state and an OFF state for each row;

a control unit configured to control the driving circuit to set a switch element on each row in an ON state for a predetermined period; and a detection circuit which detects X-ray radiation irradiation by monitoring an electrical signal output from the pixel by the control, and detects an end of X-ray radiation irradiation based on an image signal from a row corresponding to the switch element caused to continue the ON state, wherein, with a first row, a second row, a third row, and a fourth row arranged in the order named, the control unit executes control to set switch elements on the first and third rows in an ON state while setting switch elements on the second and fourth rows in an OFF state in a first period and set the switch elements on the second and fourth rows in an ON state while setting the switch elements on the first and third rows in an OFF state in a second period which does not overlap the first period, and the control unit further causes the switch element on the row which is in an ON state when the detection circuit has detected X-ray radiation irradiation to continue the ON state for a period longer than the predetermined period, and shifts the switch element on the row caused to continue the ON state when an end of the X-ray radiation irradiation is detected to an OFF state.

26. An X-ray radiation imaging system comprising:

an X-ray irradiation unit which irradiates X-ray radiation;

an imaging unit including a plurality of pixels arranged in a matrix form, a switch element connected to each pixel, and a column signal line common to pixels on each column to which each pixel is connected via the switch element;

a driving circuit which performs control to set the switch element in an ON state and an OFF state for each row;

a control unit which causes the driving circuit to set a switch element on each row in an ON state for a predetermined period so as to simultaneously set the switch elements on a plurality of rows in an ON state while inhibiting the switch elements on adjacent rows from being simultaneously set in an ON state; and a detection circuit which detects X-ray radiation irradiation by monitoring an electrical signal output from the pixel by the control, wherein the control unit causes the switch element on a row which is in an ON state when the detection circuit has detected X-ray radiation irradiation to continue an ON state for a period longer than the predetermined period.

27. An X-ray radiation imaging system comprising:

an X-ray irradiation unit which irradiates X-ray radiation;

an imaging unit including a plurality of pixels arranged in a matrix form, a switch element connected to each pixel, and a column signal line common to pixels on each column to which each pixel is connected via the switch element;

a driving circuit which performs control to set the switch element in an ON state and an OFF state for each row;

a control unit configured to cause the driving circuit to set a switch element on each row in an ON state for a predetermined period;

a detection circuit which detects X-ray radiation irradiation by monitoring an electrical signal output from the pixel by the control, and detects an end of X-ray radiation irradiation based on an image signal from a row corresponding to the switch element caused to continue the ON state, wherein, with a first row, a second row, a third row, and a fourth row arranged in the order named, the control unit executes control to set switch elements on the first and third rows in an ON state while setting switch elements on the second and fourth rows in an OFF state in a first period and set the switch elements on the second and fourth rows in an ON state while setting the switch elements on the first and third rows in an OFF state in a second period which does not overlap the first period, and the control unit further causes the switch element on the row which is in an ON state when the detection circuit has detected X-ray radiation irradiation to continue the ON state for a period longer than the predetermined period, and shifts the switch element on the row caused to continue the ON state when an end of the X-ray radiation irradiation is detected to an OFF state.

28. A method of controlling an X-ray radiation imaging apparatus including an imaging unit including a plurality of pixels arranged in a matrix form, a switch element connected to each pixel, and a column signal line common to pixels on each column to which each pixel is connected via the switch element, and a driving circuit which performs control to set the switch element in an ON state and an OFF state for each row, and a detection unit configured to detect X-ray radiation irradiation by monitoring an electrical signal output from the pixel, the method comprising:

a control step of causing the driving circuit to set a switch element on each row in an ON state for a predetermined period so as to simultaneously set the switch elements on a plurality of rows in an ON state while inhibiting the switch elements on adjacent rows from being simultaneously set in an ON state; and a detection step of detecting X-ray radiation irradiation by monitoring an electrical signal output from the pixel by the control, wherein in the control step, the switch element on a row which is in an ON state when the detection circuit has detected X-ray radiation irradiation is caused to continue the ON state for a period longer than the predetermined period.

29. A method of controlling an X-ray radiation imaging apparatus including an imaging unit including a plurality of pixels arranged in a matrix form, a switch element connected to each pixel, and a column signal line common to pixels on each column to which each pixel is connected via the switch element, and a driving circuit which performs control to set the switch element in an ON state and an OFF state for each row, comprising:

a control step of controlling the driving circuit to set a switch element on each row in an ON state for a predetermined period; and a detection step of detecting X-ray radiation irradiation by monitoring an electrical signal output from the pixel by the control, and detecting an end of X-ray radiation irradiation based on an image signal from a row corresponding to the switch element caused to continue the ON state, wherein with a first row, a second row, a third row, and a fourth row arranged in the order named, in the control step, control is executed to set switch elements on the first and third rows in an ON state while setting switch elements on the second and fourth rows in an OFF state in a first period and set the switch elements on the second and fourth rows in an ON state while setting the switch elements on the first and third rows in an OFF state in a second period which does not overlap the first period, and in the control step, the switch element on the row which is in an ON state when the detection circuit has detected X-ray radiation irradiation is caused to continue the ON state for a period longer than the predetermined period, and the switch element on the row caused to continue the ON state when an end of the X-ray radiation irradiation is detected is shifted to an OFF state.

30. A non-transitory computer-readable storage medium storing a program for causing a computer to execute steps in a method of controlling an X-ray radiation imaging apparatus including an imaging unit including a plurality of pixels arranged in a matrix form, a switch element connected to each pixel, and a column signal line common to pixels on each column to which each pixel is connected via the switch element, and a driving circuit which performs control to set the switch element in an ON state and an OFF state for each row, and a detection unit configured to detect X-ray radiation irradiation by monitoring an electrical signal output from the pixel, the method comprising:

a control step of causing the driving circuit to set a switch element on each row in an ON state for a predetermined period so as to simultaneously set the switch elements on a plurality of rows in an ON state while inhibiting the switch elements on adjacent rows from being simultaneously set in an ON state; and a detection step of detecting X-ray radiation irradiation by monitoring an electrical signal output from the pixel by the control, wherein in the control step, the switch element on a row which is in an ON state when the detection circuit has detected X-ray radiation irradiation is caused to continue the ON state for a period longer than the predetermined period.

31. A non-transitory computer-readable storage medium storing a program for causing a computer to execute steps in a method of controlling an X-ray radiation imaging apparatus including an imaging unit including a plurality of pixels arranged in a matrix form, a switch element connected to each pixel, and a column signal line common to pixels on each column to which each pixel is connected via the switch element, and a driving circuit which performs control to set the switch element in an ON state and an OFF state for each row, comprising:

a control step of controlling the driving circuit to set a switch element on each row in an ON state for a predetermined period; and a detection step of detecting X-ray radiation irradiation by monitoring an electrical signal output from the pixel by the control, and detecting an end of X-ray radiation irradiation based on an image signal from a row corresponding to the switch element caused to continue the ON state, wherein with a first row, a second row, a third row, and a fourth row arranged in the order named, in the control step, control is executed to set switch elements on the first and third rows in an ON state while setting switch elements on the second and fourth rows in an OFF state in a first period and set the switch elements on the second and fourth rows in an ON state while setting the switch elements on the first and third rows in an OFF state in a second period which does not overlap the first period, and in the control step, the switch element on the row which is in an ON state when the detection circuit has detected X-ray radiation irradiation is caused to continue the ON state for a period longer than the predetermined period, and the switch element on the row caused to continue the ON state when an end of the X-ray radiation irradiation is detected is shifted to an OFF state.

\* \* \* \* \*